United States Patent
Kikuhara et al.

(10) Patent No.: US 10,247,647 B2
(45) Date of Patent: Apr. 2, 2019

(54) CELL TRAPPING DEVICE, CELL TRAPPING SYSTEM, AND PRODUCTION METHOD FOR CELL TRAPPING DEVICE

(71) Applicant: HITACHI CHEMICAL COMPANY, LTD., Tokyo (JP)

(72) Inventors: Yoshihito Kikuhara, Tokyo (JP); Hisashige Kanbara, Tokyo (JP); Akio Kotato, Tokyo (JP); Taihei Odagiri, Tokyo (JP); Masafumi Kanetomo, Tokyo (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 366 days.

(21) Appl. No.: 14/910,869

(22) PCT Filed: Jul. 28, 2014

(86) PCT No.: PCT/JP2014/069846
§ 371 (c)(1),
(2) Date: Feb. 8, 2016

(87) PCT Pub. No.: WO2015/019889
PCT Pub. Date: Feb. 12, 2015

(65) Prior Publication Data
US 2016/0195458 A1    Jul. 7, 2016

(30) Foreign Application Priority Data
Aug. 9, 2013   (JP) .................... 2013-166407

(51) Int. Cl.
*G01N 1/40*   (2006.01)
(52) U.S. Cl.
CPC ... *G01N 1/4077* (2013.01); *G01N 2001/4088* (2013.01)

(58) Field of Classification Search
USPC ........................................ 422/534
See application file for complete search history.

(56) References Cited

U.S. PATENT DOCUMENTS 6,139,757 A * 10/2000 Ohmura .............. B01D 61/18
                                          210/351
6,750,039 B1    6/2004 Bargoot et al.
(Continued)

FOREIGN PATENT DOCUMENTS

CN    202730123 U    2/2013
CN    302490411 A    7/2013
(Continued)

OTHER PUBLICATIONS

Search Report of EP Patent Application No. 14834228.0 dated Mar. 28, 2017 in English.
(Continued)

*Primary Examiner* — Jill A Warden
*Assistant Examiner* — Brittany I Fisher
(74) *Attorney, Agent, or Firm* — Fitch, Even, Tabin & Flannery LLP

(57) ABSTRACT

A cell trapping device 1 includes: a housing 10, a filter, and a plurality of fastening members 60. The housing 10 includes: a lid member 100 having an introduction channel 101 configured to introduce a test liquid into an inside; and a storage member 200 having a discharge channel 201 configured to discharge the test liquid to an outside. The filter is provided on a channel in the housing 10 and supported between the lid member 100 and the storage member 200 by the lid member 100 and the storage member 200. The fastening members 60 configured to clamp the lid member 100 and the storage member 200 from both sides in (Continued)

an intersecting direction that is a direction intersecting with the filter to fasten the lid member 100 and the storage member 200 to each other.

17 Claims, 24 Drawing Sheets

(56) References Cited

U.S. PATENT DOCUMENTS

| | | | |
|---|---|---|---|
| 6,884,341 B2* | 4/2005 | Ferguson | G01N 1/2813 |
| | | | 137/550 |
| 6,964,646 B1* | 11/2005 | Biesel | A61M 1/3633 |
| | | | 210/252 |
| 2003/0148403 A1* | 8/2003 | Nakajima | B01L 3/5025 |
| | | | 506/33 |
| 2004/0014023 A1* | 1/2004 | Meserol | C12Q 1/001 |
| | | | 435/2 |
| 2005/0070012 A1* | 3/2005 | Muraishi | B01L 3/502 |
| | | | 435/287.2 |
| 2005/0195684 A1* | 9/2005 | Mayer | B01D 61/18 |
| | | | 366/197 |
| 2006/0073585 A1* | 4/2006 | McDevitt | C12Q 1/04 |
| | | | 435/288.7 |
| 2011/0053152 A1 | 3/2011 | Goldkorn et al. | |

FOREIGN PATENT DOCUMENTS

| | | |
|---|---|---|
| CN | 302505822 S | 7/2013 |
| JP | H5-025918 A | 4/1993 |
| JP | H8-163997 A | 6/1996 |
| JP | 2003-070904 A | 3/2003 |
| JP | 2005-106536 A | 4/2005 |
| JP | 2008-532539 A | 8/2008 |
| JP | 2008-537485 A | 9/2008 |
| JP | 2011-163830 A | 8/2011 |
| JP | 2013-138658 A | 7/2013 |
| WO | 2010/135603 A2 | 11/2010 |
| WO | 2013/103144 A1 | 7/2013 |

OTHER PUBLICATIONS

Hosokawa, M. et al., "Size-based isolation of circulating tumor cells in lung cancer patients using a microcavity array systemn," PLOS One, Jun. 2013 vol. 8 No. 6 e67466, p. 1-p. 9.

Hosokawa, M. et al., "Microcavity array system for size-based enrichment of circulating tumor cells from the blood of patients with small-cell lung cancer," Anal. Chem., May 2013 vol. 85, p. 5692-p. 5698.

Hosokawa, M. et al., "Size-selective microcavity array for rapid and efficient detection of circulating tumor cells," Anal. Chem., 2010 vol. 82, p. 6629-p. 6635.

Negishi, R. et al., "Development of the automated circulating tumor cell recovery system with microcavity array," URL:http://dx.doi.org/10.1016/j.bios.2014.09.002i, Biosensors and Bioelectronics, Sep. 2014, p. 1-p. 5.

Negishi, R. et al., "Development of automated recovery system of circulating tumor cells using a microcavity array," 2014 Nen The Electrochemical Society of Japan Dai 81 Kai Taikai Koen Yoshishu, Mar. 2014, p. 237 1N02.

Negishi, R. et al., "Development of automated collection system for circulating tumor cells using a microcavity array," Abstracts of the Annual Meeting of the Society for Biotechnology, Japan, Aug. 2013, p. 151-p. 2P-189.

International Search Report for PCT/JP2014/069846 dated Oct. 21, 2014; English translation submitted herewith (5 pages).

International Preliminary Report on patentability (IPRP) for WO Patent Application No. PCT/JP2014/069846 dated Feb. 18, 2016 in English.

Masahito Hosokawa et al., "Size-Based Isolation of Circulating Tumor Cells in Lung Cancer Patients Using a Microcavity Array System", PLOS One, Jun. 28, 2013 in English.

Office Action of CN Patent Application No. 201480044965.9 dated Aug. 26, 2016.

* cited by examiner

Fig.9
(A)
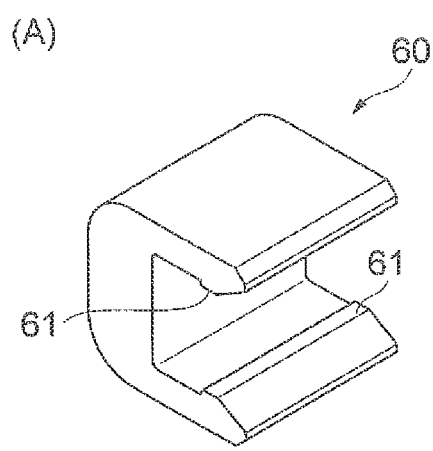
(B)
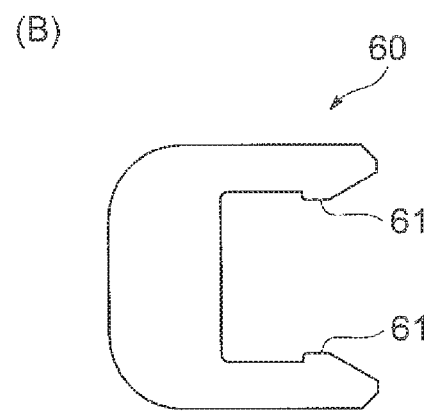

Fig.11
(A) 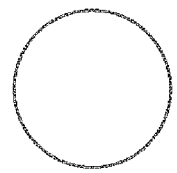
(B) 
(C) 
(D) 
(E) 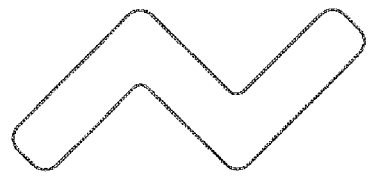
(F) 

Fig.23
(A)
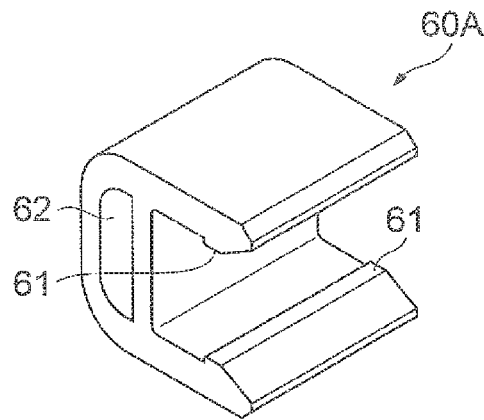
(B)
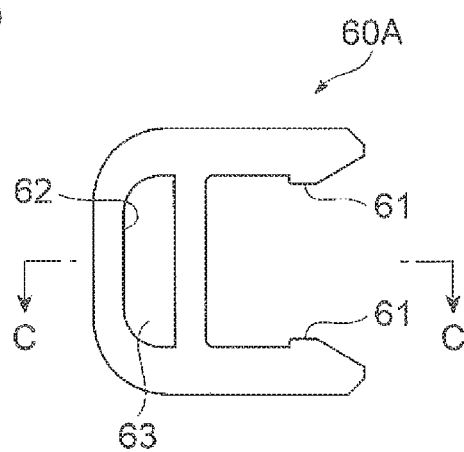
(C)
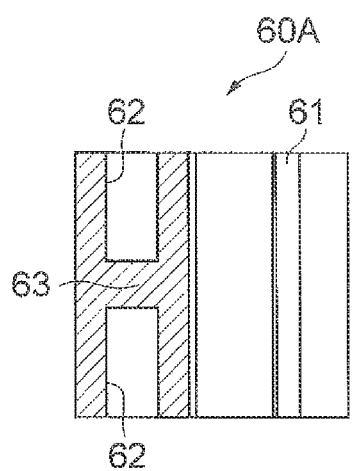

CELL TRAPPING DEVICE, CELL TRAPPING SYSTEM, AND PRODUCTION METHOD FOR CELL TRAPPING DEVICE

TECHNICAL FIELD

The present invention relates to a cell trapping device to trap tumor cells contained in a cell dispersion, a cell trapping system using this cell trapping device, and a method for producing the cell trapping device.

BACKGROUND ART

Cancer is the major cause of death in the world. In Japan, more than 300,000 people per year die of cancer, and thus the early detection and the treatment of cancer are desired. In most cases, the death of humans due to cancer is caused by metastatic recurrence of cancer. The metastatic recurrence of cancer is caused by fixing and infiltrating tumor cells from a primary lesion through blood vessels or lymph vessels to the blood vessel wall of another organ tissue to form micrometastases. The tumor cell circulating in a human body through blood vessels or lymph vessels as described above is called Circulating Tumor Cell (hereinafter, may be called "CTC").

In blood, many blood cell components such as red blood cells, white blood cells, and platelets are included, and the number thereof is said to be $3.5 \times 10^9$ pieces to $9 \times 10^9$ pieces in 1 mL of blood. On the contrary, only several numbers of CTCs exist, and thus the blood is needed to be filtered in order to efficiently trap and detect CTCs from the blood cell components. Various studies have been made on such a device. For example, Patent Literature 1 has disclosed a microfluidic devices provided with a polydimethylsiloxane (PDMS) upper member provided with a sample supply ports located at the upper part and the lower part of a nickel substrate having fine through-holes in the nickel substrate and a lower member provided with a sample discharge port.

In addition to the performance to trap and detect CTCs, such a device is required to be easily disassembled in order to take out the detected CTCs from the device. As a device having improved disassembly property, Patent Literature 2 has disclosed a filter unit for biological component separation that solves problems such as labor at the time of disassembly of the filter after use and breakage of the filter, does not cause blood leakage at the circumference of the filter unit, and has an excellent handling property. Patent Literature 3 has disclosed a cell trapping device in which a housing is tightly fixed by joint in order to enable the trapped CTCs to be observed without disassembling the device.

CITATION LIST

Patent Literature

Patent Literature 1: Japanese Unexamined Patent Publication No. 2011-163830
Patent Literature 2: Japanese Unexamined Patent Publication No. 2003-70904
Patent Literature 3: Japanese Unexamined Patent Publication No. 2013-138658

SUMMARY OF INVENTION

Technical Problem

However, in the filter unit for biological component separation disclosed in Patent Literature 2, a lid member and a storage member are fastened by pressure using clamps in order to prevent the leakage of blood and thus the repeatability of the support balance of the filter in each pressure fastening tends to be poor. The repeatability of the support balance of the filter affects the repeatability of biological component separation. In the cell trapping device disclosed in Patent Literature 3, the device should be disassembled when CTCs are used for experiment (for example, to culture) by taking out CTCs whose trap is ascertained by observation from the filter and thus the trapped CTCs may be scattered by impact at the time of disassembly.

The present invention has been made in view of the above problems and a purpose of the present invention is to provide a cell trapping device that is easy to disassemble and has improved repeatability of the support balance of the filter. Another purpose of the present invention is to provide a cell trapping system provided with this device and a method for producing the cell trapping device.

Solution to Problem

In order to achieve the purpose, a cell trapping device according to one aspect of the present invention is a cell trapping device configured to trap cells in a test liquid, the device including: a housing having a lid member having an introduction channel configured to introduce a test liquid into an inside and a storage member having a discharge channel configured to discharge the test liquid to an outside; a filter having a filter region in which a through-hole configured to pass the test liquid is formed inside the filter in a thickness direction, provided on a channel between the introduction channel and the discharge channel in the housing, and supported between the lid member and the storage member by the lid member and the storage member, and a plurality of fastening members configured to clamp the lid member and the storage member from both sides in an intersecting direction that is a direction intersecting with the filter to fasten the lid member and the storage member to each other, in which the fastening members are located along a peripheral edge part of the housing so as to surround the filter.

A method for producing the cell trapping device according to one aspect of the present invention is a method for producing a cell trapping device including a housing having a lid member having an introduction channel configured to introduce a test liquid into an inside and a storage member having a discharge channel configured to discharge the test liquid to an outside; a filter having a filter region in which a through-hole configured to pass the test liquid is formed inside the filter in a thickness direction, provided on a channel between the introduction channel and the discharge channel in the housing, and supported between the lid member and the storage member by the lid member and the storage member; and a plurality of fastening members configured to clamp the lid member and the storage member from both sides in an intersecting direction that is a direction intersecting with the filter to fasten the lid member and the storage member to each other, the method including: overlapping the storage member, the filter, and the lid member; and clamping the peripheral part of the housing by the fastening members so as to surround the filter.

According to the cell trapping device and the method for producing the cell trapping device, the lid member and the storage member are fastened by the fastening members from both sides in the intersecting direction that is the direction intersecting with the filter. The fastening members are located along the peripheral edge part of the housing so as to surround the filter and thus the filter can be fastened by a predetermined load through the peripheral edge part of the housing. This improves the repeatability of the support balance of the filter. In the stage of taking out the detected cells from the device, the lid member is easily detached from the storage member by removing the fastening members. This can reduce the impact applied to the filter at the time of detaching the lid member from the storage member, and thus the risk of the scatter of the cells trapped in the filter is reduced. In other word, the cell trapping device according to the one aspect of the present invention can be easily disassembled in such a degree that the disassembly does not cause the trouble in the workability at the collection stage of the cells.

Preferably, at least one of the lid member and the storage member includes guide parts extending along an outer edge of a surface at a peripheral edge part of the surface to be an outer surface in the intersecting directions at the time of assembly, the fastening members include claws protruding from a surface facing to the surface including the guide parts, and the fastening members be configured to be slidable along the guide parts by engaging the claws with the guide parts. This allows each fastening members to be attached and detached only in a direction along each guide part and thus unexpected detachment of the fastening members can be prevented.

The guide parts may be protrusions. In this case, the guide parts can be provided without thinning the entire housing. Also, the guide parts may be grooves. In this case, the guide parts can be provided without thickening the entire housing.

It is preferable that the cell trapping device further include a supporting member configured to support the filter between the lid member and the storage member, the lid member or the storage member have a groove having a depth in the intersecting direction at a position of an outer side from the filter region at the time of assembly, the supporting member have a shape that allows the supporting member to be accommodated in the groove, and the supporting member accommodated in the lid member or the storage member support the filter by pressing the filter to the groove side of the lid member or the storage member at an outer circumference side from the filter region. In this aspect, the filter is supported by pressing the filter by the groove part that the lid member or the storage member has and the supporting member accommodated in the groove part and thus the position of the filter is difficult to move at the time of detaching the lid member form the storage member. Consequently, the risk of the scatter of the cells trapped in the filter is further reduced.

In addition, it is preferable that the lid member of the cell trapping device include: a first protrusion part provided at a position outward from the filter region and inward from an outer edge of the filter at the time of assembly and to protrude outward from a surface of a side to which the filter is attached; and a first fitting part provided at a position outward away from the first protrusion part and a position where at least a part of the filter is overlapped at the time of assembly and configured to fit with the storage member, the storage member include: a second protrusion part provided at a position corresponding to the first protrusion part at the time of assembly and located at a position corresponding to the first protrusion part to protrude; and a second fitting part configured to fit with the lid part at the time of assembly, one of the first fitting part and the second fitting part have a convex shape and the other have a concave shape, and the channel be formed inside the housing by locating the first protrusion part and the second protrusion part at a corresponding position sandwiching the filter and the filter is fastened by fitting the first fitting part and the second fitting part at an outer circumference side from the filter region.

In the above aspect, the filter is fastened by the first protrusion part of the lid member and the second protrusion of the storage member and, by fitting the first fitting part and the second fitting part located at further outside, the outer circumference part of the filter is sandwiched therebetween. This result in fastening the filter between the lid member and the storage member with the filter being pulled from the center of the filter to the outward direction and thus the filter does not generate wrinkles or the like. Consequently, the cells contained in the test liquid passing through the filter region located inside the filter can be suitably trapped. In addition, the filter is sandwiched by the first protrusion part and the second protrusion part from both sides at the position to be the outer circumference side of the filter region, and thus the channel of the liquid is blocked from the outside and diffusion of the liquid through the filter and other components in the device can be prevented when the liquid (test liquid or treatment liquid) is introduced to the inside of the cell trapping device. This results in preventing seepage of the liquid to the outside. Consequently, the cells in the test liquid can be trapped at the filter region and the trapped cells can be easily and precisely observed without disassembling the device. The filter is fastened by fitting with the first protrusion part and the second protrusion part and thus the filter can be fastened in a state of reduction in fluctuation of the height of the filter surface. This allows the workability at the time of microscopic observation of the cells to be improved.

It is preferable that the cell trapping device further include a sealing member configured to be sandwiched between the filter and at least one of the first protrusion part and the second protrusion part and to have elasticity, and the sealing member may be located at all regions corresponding to the first protrusion part and the second protrusion part in a state of sandwiching the filter. This results in improved blocking property of the channel inside of the housing.

It is preferable that an outer surface of the storage member protrude in the intersecting direction, compared with an edge part of the storage member side of the fastening members. This can maintain the observation stage and the filter in parallel when, for example, the filter is supported parallel to the outer surface of the storage member at the time of microscopic observation of the trapped cells without detaching the fastening members and thus the workability at the time of microscopic observation is improved. It is preferable that an outer surface of the lid member protrude in the intersecting direction compared with an edge part of the lid member side of the fastening members. This makes the fastening members not obstacle to an objective lens in the relative movement of the housing and the objective lens and thus the workability at the time of microscopic observation is improved. It is preferable that a length of the fastening members in the intersecting direction be equal to or less than the thickness of the housing. In this case, improvement of the workability at the time of the microscopic observation is easy to achieve.

It is preferable that the filter in the cell trapping device have a plurality of alignment holes at positions outward from the filter region and inward from an outer edge of the filter and at least one of the lid member and the storage member have hole parts provided at positions corresponding to the alignment holes. As the method for producing the cell trapping device, it is preferable that the filter have a plurality of alignment holes at positions outward from the filter region and inward from an outer edge of the filter and at least one of the lid member and the storage member have hole parts provided at positions corresponding to the alignment holes, and the method include aligning the lid member or the storage member and the filter by inserting stick-like jigs whose edge parts are inserted into the hole parts through the alignment holes at the time of overlapping the filter with the lid member or the storage member. This results in improving the alignment of the filter and at least one of the lid member and the storage member and thus the repeatability of the support balance of the filter can be further improved.

The test liquid introduced into the cell trapping device according to one aspect of the present invention may be blood and the trapped cells may be circulating tumor cells. The cell trapping device according to one aspect of the present invention is particularly suitable for trapping the circulating tumor cells in blood.

A cell trapping system according to one aspect of the present invention includes: the cell trapping device; test liquid supplying means for supplying the test liquid to the introduction channel of the cell trapping device; treatment liquid supplying means for supplying the treatment liquid for treating the cells trapped in the filter to the introduction channel of the cell trapping device by passing the treatment liquid through the filter; and selecting means for selecting the liquid to supply to the cell trapping device from the test liquid and the treatment liquid.

According to the cell trapping system, the trapping process of the cells in the test liquid can be effectively carried out compared with conventional systems by having the configuration of selecting the supplied liquid to the cell trapping device by the selection means and, based on the selection result, supplying the test liquid or the treatment liquid to the cell trapping device.

Advantageous Effects of Invention

According to the present invention, the cell trapping device being easy to disassemble and having the improved repeatability of the support balance (almost equal pressure is applied) of the filter can be provided. In addition, the cell trapping system provided with this cell trapping device and the method for producing the cell trapping device can be provided.

BRIEF DESCRIPTION OF DRAWINGS

FIG. 9(A) is a perspective view and FIG. 9(B) is a plane view of the fastening member.
FIG. 11 is a view illustrating other examples of the shapes of a through-hole provided in the filter.
FIG. 23 is a view illustrating a modified example of the fastening member.

DESCRIPTION OF EMBODIMENTS

Hereinafter, configurations for carrying out the present invention will be described in detail with reference to the attached drawings. In the description of the drawings, the same sign is assigned to the same element and redundant descriptions are omitted.

(Cell Trapping Device)

Figure 1:
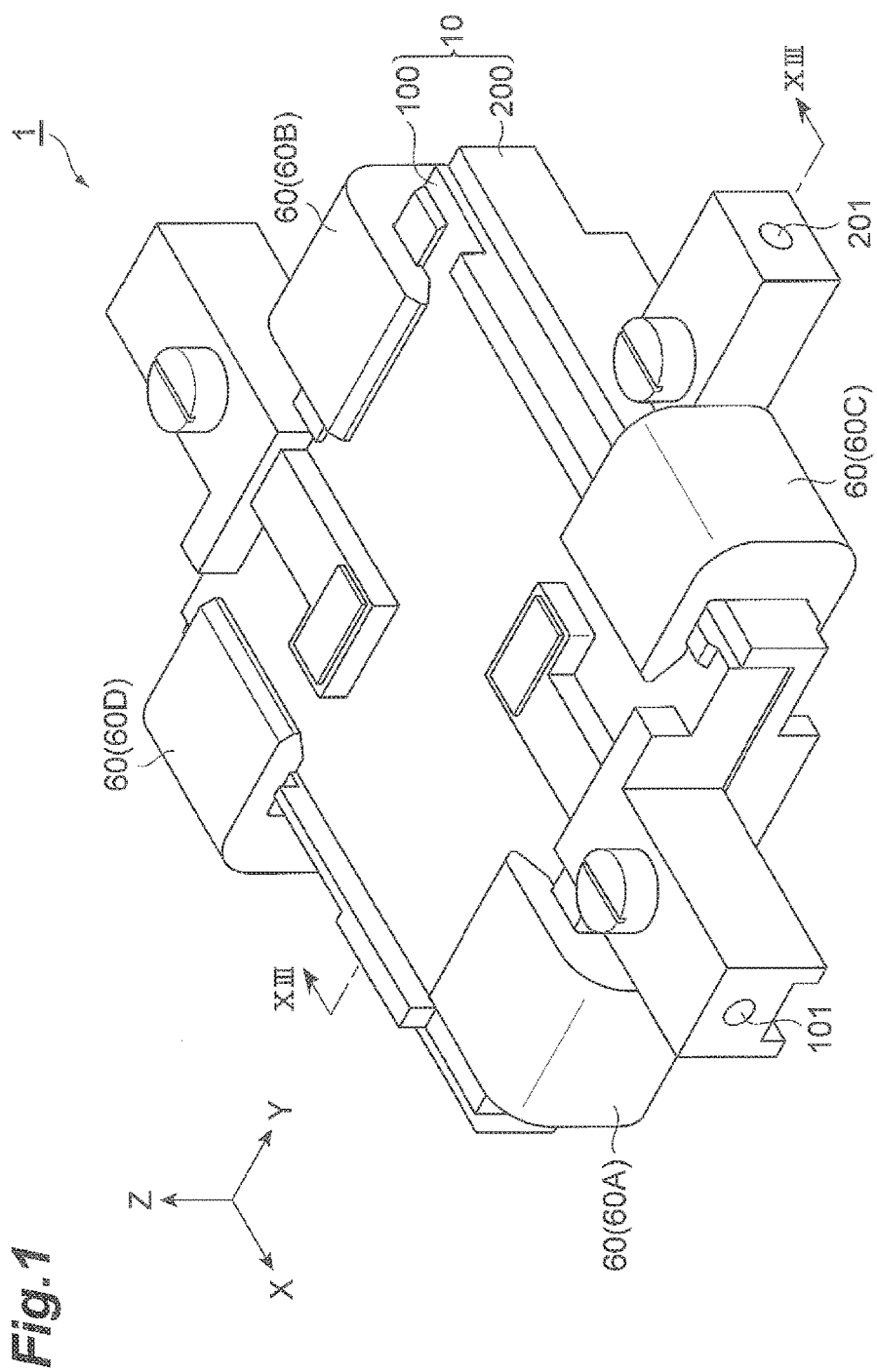
FIG. 1 is a schematic perspective view illustrating the configuration of a cell trapping device.
Figure 2:
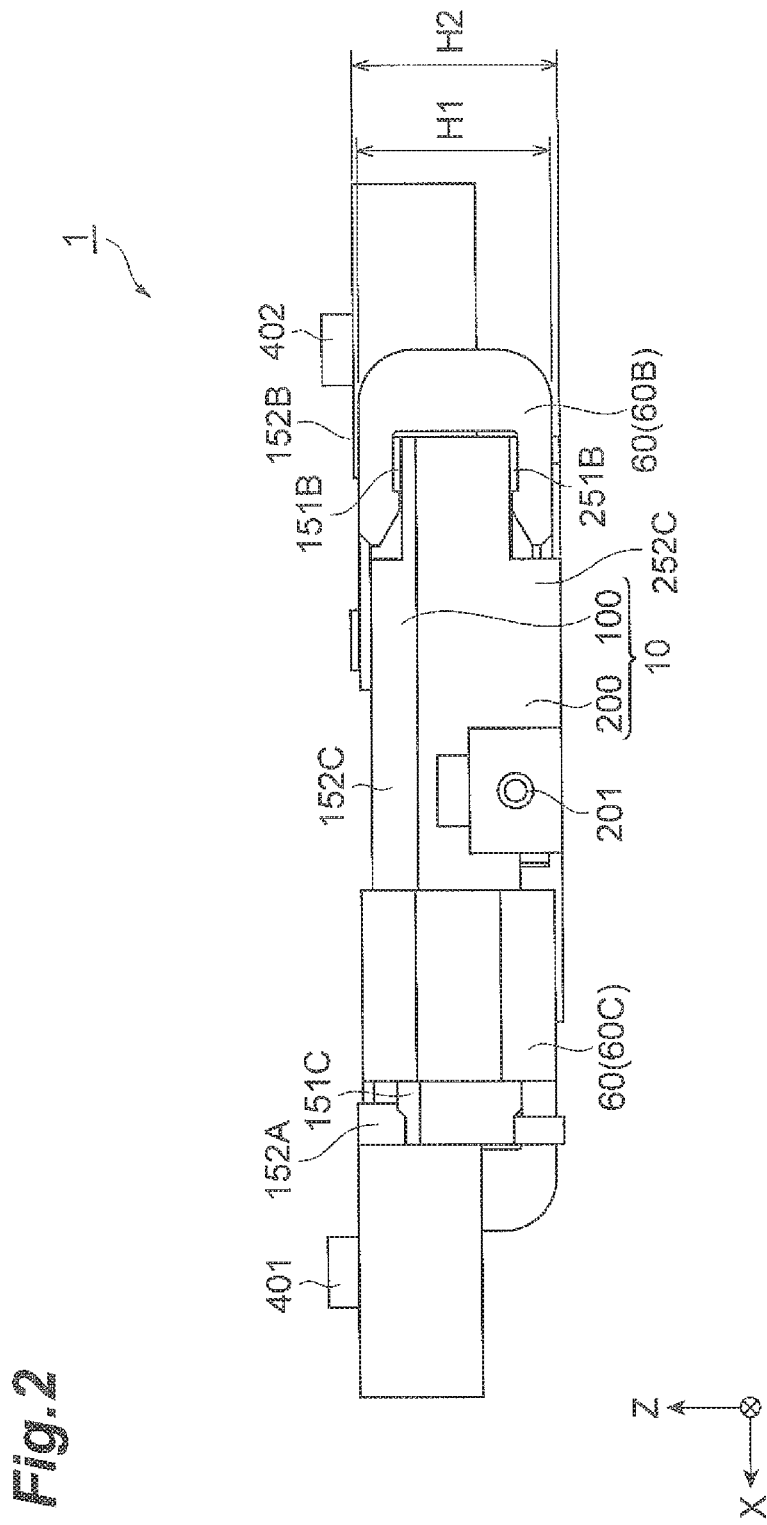
FIG. 2 is a side view of the side having a discharge channel of FIG. 1.

FIG. 1 is a schematic perspective view illustrating the configuration of a cell trapping device according to an embodiment of the present invention and FIG. 2 is a side view of the side having the discharge channel of FIG. 1. The cell trapping device 1 illustrated in FIG. 1 has a function for trapping specific cells in a biological liquid with a filter provided inside the cell trapping device 1. As a particularly preferable example, the cell trapping device 1 has a function that red blood cells, white blood cells, and platelets (hereinafter, these are collectively called "blood cell components") contained in the blood are passed and circulating tumor cells called CTCs are trapped from blood containing the CTCs. The cells trapped with the filter are observed with a microscope or the like after applying staining treatment by introducing a washing liquid, a staining liquid, and the like into the device.

The cell trapping device 1 shown in FIG. 1 is provided with a housing 10 and a filter through which a test liquid passes provided inside the housing 10. The test liquid is a liquid in which cells are dispersed. The housing 10 is configured to include a lid member 100 and a storage member 200. The dimension and the shape of the part surrounded with a lid member side guide parts and a storage member side guide parts are preferably approximately square shape having a one side length of 10 mm to 100 mm in a plane view from the viewpoint of workability and observability. The one side length is preferably 15 mm to 70 mm and further preferably 20 mm to 30 mm. The thickness of the housing 10 (corresponding to H2 in FIG. 2) is preferably 2 mm to 20 mm, more preferably 3 mm to 15 mm, and further preferably 5 mm to 10 mm from the viewpoint of the movable range in the height direction of observation equipment.

The lid member 100 and the storage member 200 are fastened to each other by clamping them from both sides in an overlapped direction (intersecting direction of the filter) with four fastening members 60 (60A to 60D). The four fastening members 60 are located at the peripheral edge part of the housing 10 so as to surround the filter.

As the material for the lid member 100 and the storage member 200, a material having relatively high rigidity is preferably selected. This allows deformation caused by applying pressure at the time of assembling and fastening the cell trapping device 1 to be reduced. However, use of a material having excessively high rigidity generates scratches of the filter when stress is applied to the fitting part. The rigidity of the material can be represented by, for example, Young's modulus. Consequently, as the material of the lid member 100 and the storage member 200, a material having Young's modulus at room temperature of 0.1 GPa to 100 GPa is preferable and that of 1 GPa to 10 GPa is more preferable. Young's modulus can be measured by generally known Ewing's method.

The lid member 100 is preferably made of a material having translucency to the light having a wavelength used at the time of detecting the cells that are targets of observation, particularly the light having a visible wavelength region. Examples of the material for the lid member 100 may include glass, quartz glass, plastics (particularly, acrylic resins), and macromolecules such as polydimethylsiloxane. The material, however, is not limited to these materials. The lid member 100 and the storage member 200 are not necessarily made of the same material. However, the materials are preferably the same material from the viewpoint that the stress applied to the fitting part at the time of the assembly is equally applied to the lid member side and the storage member side. As the materials for the lid member 100 and the storage member 200, an acrylic resin having low autofluorescence property is preferable and poly(methyl methacrylate) is particularly preferable because this material enables the device to be produced in a large quantity. Generally, when tumor cells are observed, staining treatment is carried out to the target cells with a fluorescence reagent and thereafter the treated cells are irradiated with the light having a wavelength of ultraviolet or visible light of 300 nm to 800 nm to carry out fluorescence observation. Therefore, as the lid member 100, a material having low autofluorescence is preferably selected so that the material itself does not emit light at the time of irradiation with the light having the wavelength (this phenomenon is called "low autofluorescence property"). Generally, organic macromolecules having aromatic rings such as a polystyrene resin and a polycarbonate resin have a high autofluorescence property and thus these macromolecules are not suitable for the above purpose in many cases.

Figure 5:
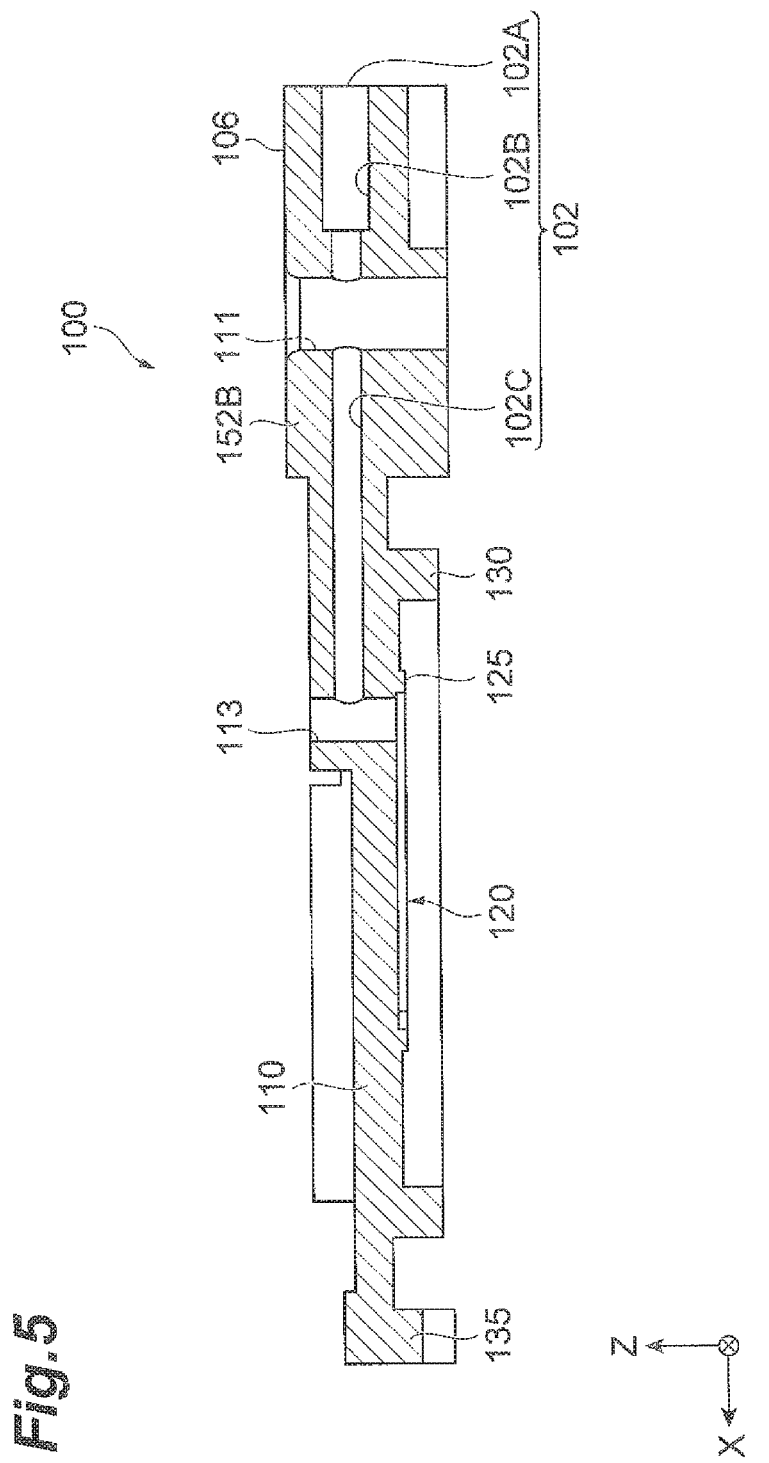
FIG. 5 is a view illustrating the inner structure of the lid member and an arrow view of the V-V section in FIG. 3.

The lid member 100 has introduction channels 101 and 102 for introducing the test liquid containing the cells to be observation target and the treatment liquid for staining treatment of the cells trapped on the filter into the inside (also refer to FIG. 5). The storage member 200 has a discharge channel 201 for discharging the test liquid from the inside to the outside. In the following description, a direction of attaching the introduction channels 101 and 102 is defined as an X axis direction, a horizontal direction orthogonal to the X axis is defined as a Y axis direction, and a vertical direction orthogonal to the X axis and Y axis is defined as a Z axis direction.

Subsequently, the configuration of the cell trapping device 1 will be described in detail. First, each configuration of the lid member 100, the storage member 200, the fastening members 60, and the filter will be described and thereafter the cell trapping device formed by assembling these components will be described.

(Lid Member)

Figure 3:
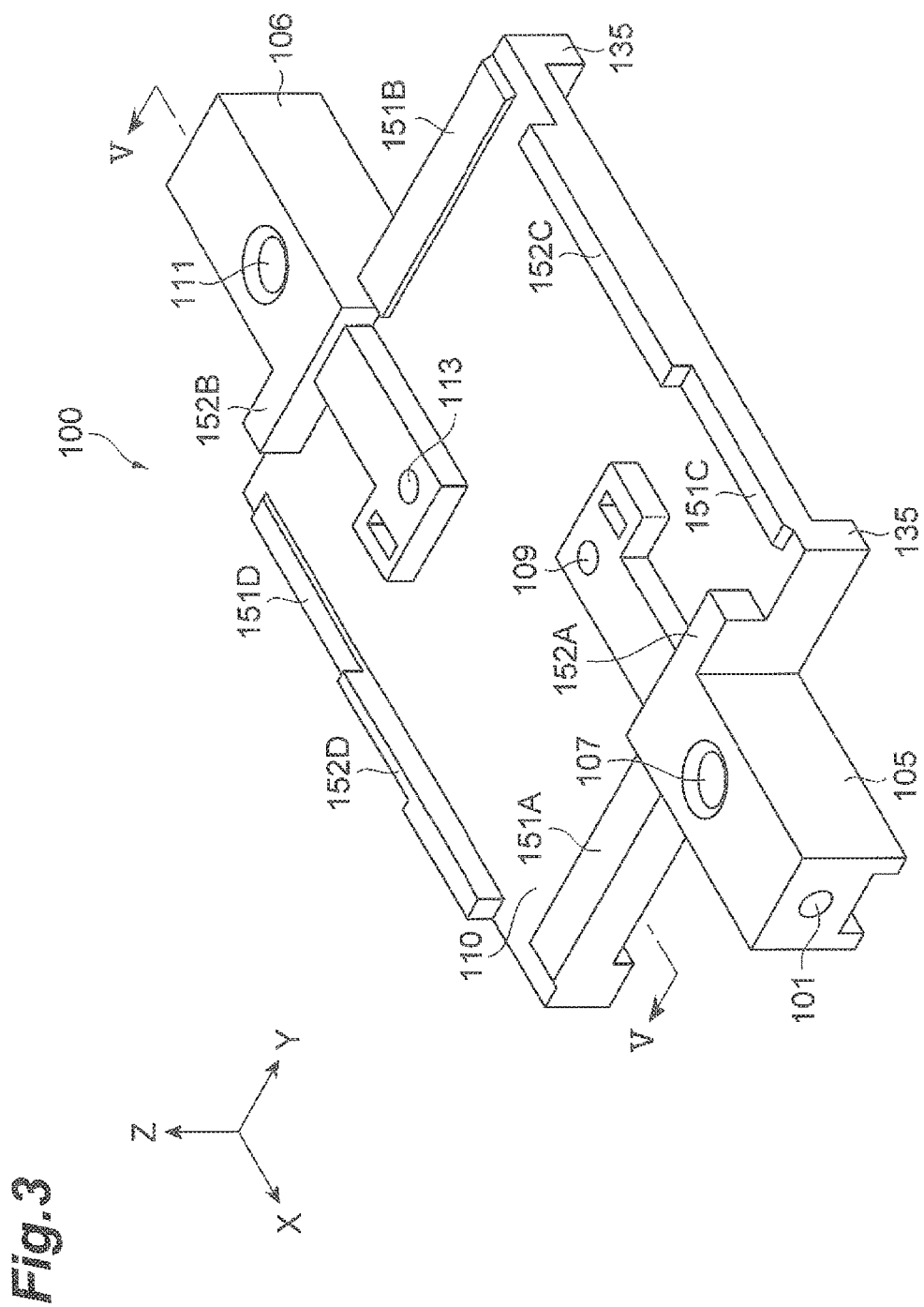
FIG. 3 is a schematic perspective view of a lid member seen from above.
Figure 4:
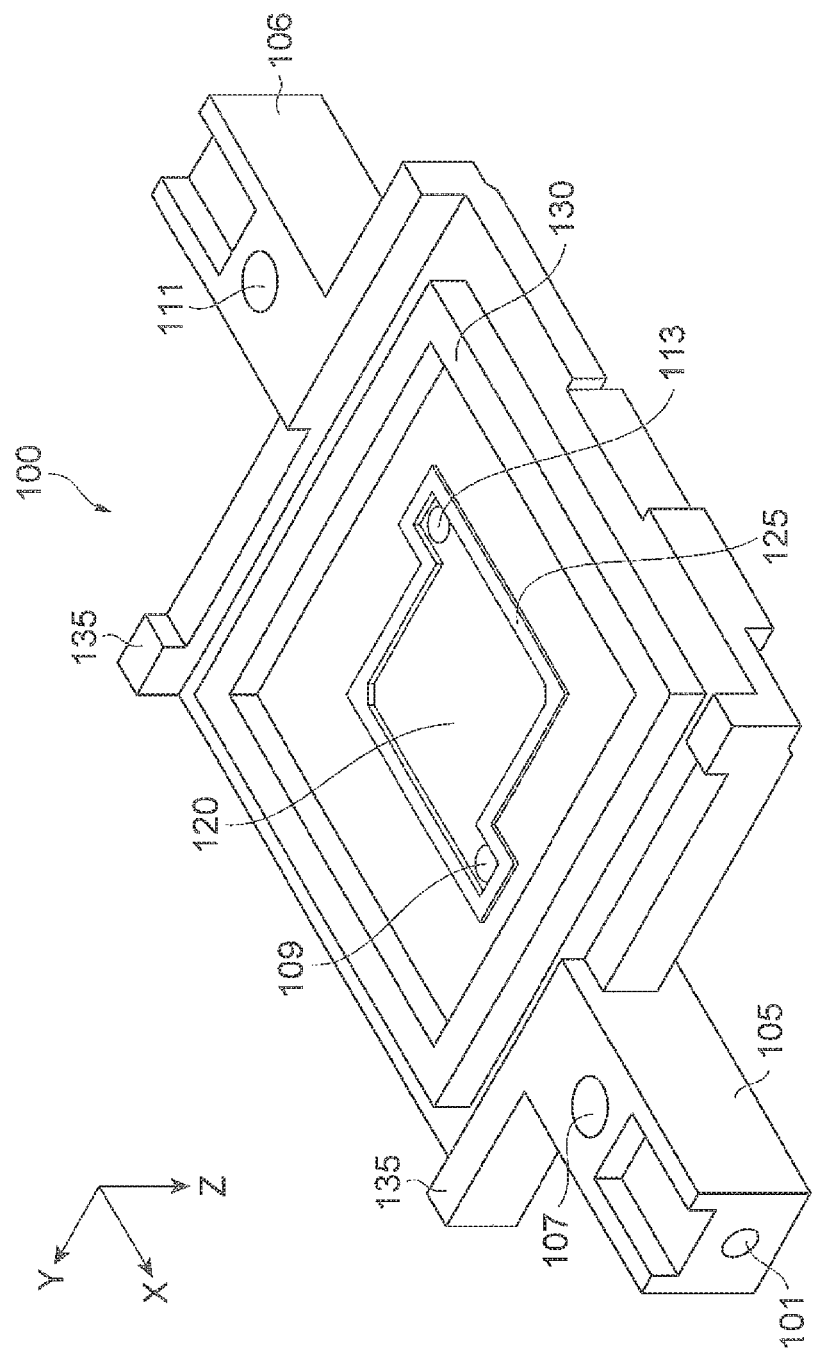
FIG. 4 is a schematic perspective view of the lid member seen from below.

First, the lid member 100 will be described. FIGS. 3 to 5 are views illustrating the configuration of the lid member 100. FIG. 3 is a schematic perspective view of the lid member 100 seen from above. FIG. 4 is a schematic perspective view of the lid member 100 seen from below. FIG. 5 is an arrow view of the V-V section in FIG. 3.

As illustrated in FIGS. 3 to 5, in the lid member 100, two channel parts 105 and 106 are attached to a main body part 110 made of a plate member having an approximately square shape so as to protrude along the X axis direction from a side edge of the main body part 110 to the outside. The channel parts 105 and 106 are attached at a position apart from the center along the Y axis direction so that the channel parts 105 and 106 are located at different positions with each other when the lid member 100 is seen from the X axis direction. Here, the channel part 106 illustrated in FIG. 5 will be described. The channel part 105, however, has a similar configuration.

In the lid member 100, an introduction region 120 made of concave space in order that the test liquid passes through the filter is provided. The introduction region 120 is provided in the upper position of the filter region in the filter so that the region providing a through-hole in the filter attached between the lid member 100 and the storage member 200 is included when the cell trapping device 1 is seen from above. To the corners of the introduction region 120, the introduction channels 101 and 102 are connected through the perforations 109 and 113 for connection. The introduction region 120 is a space for guiding the test liquid or the treatment liquid introduced from the introduction channels 101 and 102 to the through-hole of the filter.

Here, the introduction channel 102 will be further described using FIG. 5. The channel part 106 is provided with the introduction channel 102 extending along the X axis inside the channel part 106. The introduction channel 102 is configured to include an introduction opening 102A, a channel 102B extending from the introduction opening 102A to the inside, and a channel 102C connecting to the channel 102B and having a smaller hole diameter than the hole diameter of the channel 102B. In addition, a perforation 111 passing through the channel part 106 in the vertical direction (Z axis direction) is provided between the channel 102B and the channel 102C (on the other hand, a perforation 107 is provided in the channel part 105). In the perforation 111, a valve provided with a perforation functioning as a channel opening and closing valve (channel opening and closing mechanism) is inserted. This allows the opening and closing of the channel to be carried out by this channel 102B. A perforation 113 for connecting the introduction region 120 and the introduction channel 102 is provided at the edge part of the introduction channel 102 in the main body part 110 side so as to communicate to the introduction channel 102.

This allows the liquid (the test liquid or the treatment liquid) introduced from the introduction opening 102A to be transferred to the introduction region 120 through the channel 102B, the channel 102C, and the perforation 113.

At the peripheral edge of the introduction region 120, a first protrusion part 125 for preventing the liquid introduced into the introduction region 120 from leaking outside is provided so as to extending from the main body part 110 toward the lower position. As illustrated in FIG. 4, when the lid member 100 is seen from below, the first protrusion part 125 has an approximately quadrilateral shape in XY plane and has a shape in which, like a two-blade wind turbine, only the region connected to the perforations 109 and 113 passing through the introduction channels 101 and 102 protrudes from the outer circumference of the quadrilateral shape. Here, an excessively narrow width of the contact surface of the first protrusion part 125 and the filter 30 described below results in an insufficient plane, whereas an excessively wide width results in no liquid sealing effect due to excessively low surface pressure. Consequently, the width of the first protrusion part 125 is preferably 0.1 mm to 2 mm and more preferably 0.5 mm to 1 mm. The high height of the first protrusion part 125 can increase the pressure at the time of sandwiching the filter and thus the seepage prevention effect of the liquid can be improved. However, the excessively high height of the protrusion part results in increase in the thickness of the whole cell trapping device 1. This may cause trouble in observation operation of the cell trapping device and thus the thickness is preferably 0.05 mm to 1 mm and more preferably 0.1 mm to 0.8 mm.

A first fitting part 130 made of a convex part having a quadrilateral shape is formed so that the first fitting part 130 is provided away from the first protrusion part 125 and surrounds the peripheral edge of the first protrusion part 125. Form the viewpoint of the strength of the lid member 100 and the fitting property to the filter 30, the length of the one side of the first fitting part 130 in the X axis direction or the Y axis direction is preferably 8 mm to 30 mm, more preferably 10 mm to 25 mm, and further preferably 15 mm to 20 mm. The width of the convex part configuring each side of the first fitting part 130 is preferably 1 mm to 5 mm, more preferably 1 mm to 3 mm, and further preferably 1.5 mm to 2 mm. As illustrated in FIG. 5, the height of the first fitting part 130 is higher than that of the first protrusion part 125. In addition, only in the side extending along the Y axis direction in the outer edge of the main body part 110, alignment protrusion parts 135 protruding toward the lower position (toward the upper position in FIG. 4) are provided so as to be connected to the channel parts 105 and 106. These alignment protrusion parts 135 are used for aligning and orienting the lid member 100 and the storage member 200 at the time of assembling the cell trapping device 1.

As illustrated in FIG. 3, in the main body part 110 having approximately square shape, a lid member side guide parts 151 (151A to 151D) extending in an anti-clockwise direction in the plane view along the peripheral edge parts from respective end (respective corner) as a starting point are provided at the four-side peripheral edge parts of the surface to be an upper surface at the time of assembly. The lid member side guide parts 151 are protrusions protruding toward the upper position of the lid member 100 and define a direction where the fastening members 60 slide by engaging the claws of the fastening members 60 described below with the lid member side guide parts. Among the four peripheral edge parts, each of the lid member side guide parts 151A and 151B is attached to the side having longer distance in the peripheral edge parts segmentalized with the channel parts 105 and 106 in the peripheral edge parts attaching the channel parts 105 and 106 at the side edge. In other words, the lid member side guide part 151A and the lid member side guide part 151B are provided at positions diagonal with respect to the center of the main body part 110 in a plane view. On the other hand, in the remaining peripheral edge parts not attaching the channel parts 105 and 106, each of the lid member side guide parts 151C and 151D is provided in the side where a channel part that is one of the channel parts 105 and 106 located at the front side is attached (in the case of FIG. 2, the left side in the drawing) when the main body part 110 is seen from the Y axis direction. In other words, the lid member side guide part 151C and lid member side guide part 151D are provided at positions diagonal with respect to the center of the main body part 110 in a plane view. As illustrated in FIG. 3, the stepped parts of the starting points of the lid member side guide parts 151A to 151D and the upper surface of the main body part 110 are chamfered obliquely.

The lid member side guide parts 151 (151A to 151D) extend from the positions close to the edge part of the main body part 110 as the starting point to an approximately center part in each peripheral edge part of the main body part 110. From the approximately center part, lid member side stoppers 152 (152A to 152D) are continuously provided and continuously extend along the peripheral edge parts. The lid member side stoppers 152A to 152D are protrusions having higher height than the height of the lid member side guide parts 151A to 151D and define limit positions where the fastening members 60 described below slide along the lid member side guide parts 151A to 151D. The lid member side stoppers 152A to 152D extend to the positions close to the edge parts opposite to the starting points of the lid member side guide parts 151A to 151D in each peripheral edge part. The parts of the lid member side stoppers 152A and 152B in the peripheral edge parts attaching the channel parts 105 and 106 are integrated with the base parts of the channel parts 105 and 106.

The widths of the lid member side guide parts 151A and 151B and the lid member side stoppers 152A and 152B in the X axis direction are set to be larger than the widths of the lid member side guide parts 151C and 151D and the lid member side stoppers 152C and 152D in the Y axis direction. This reason will be described below.

(Storage Member)

Figure 6:
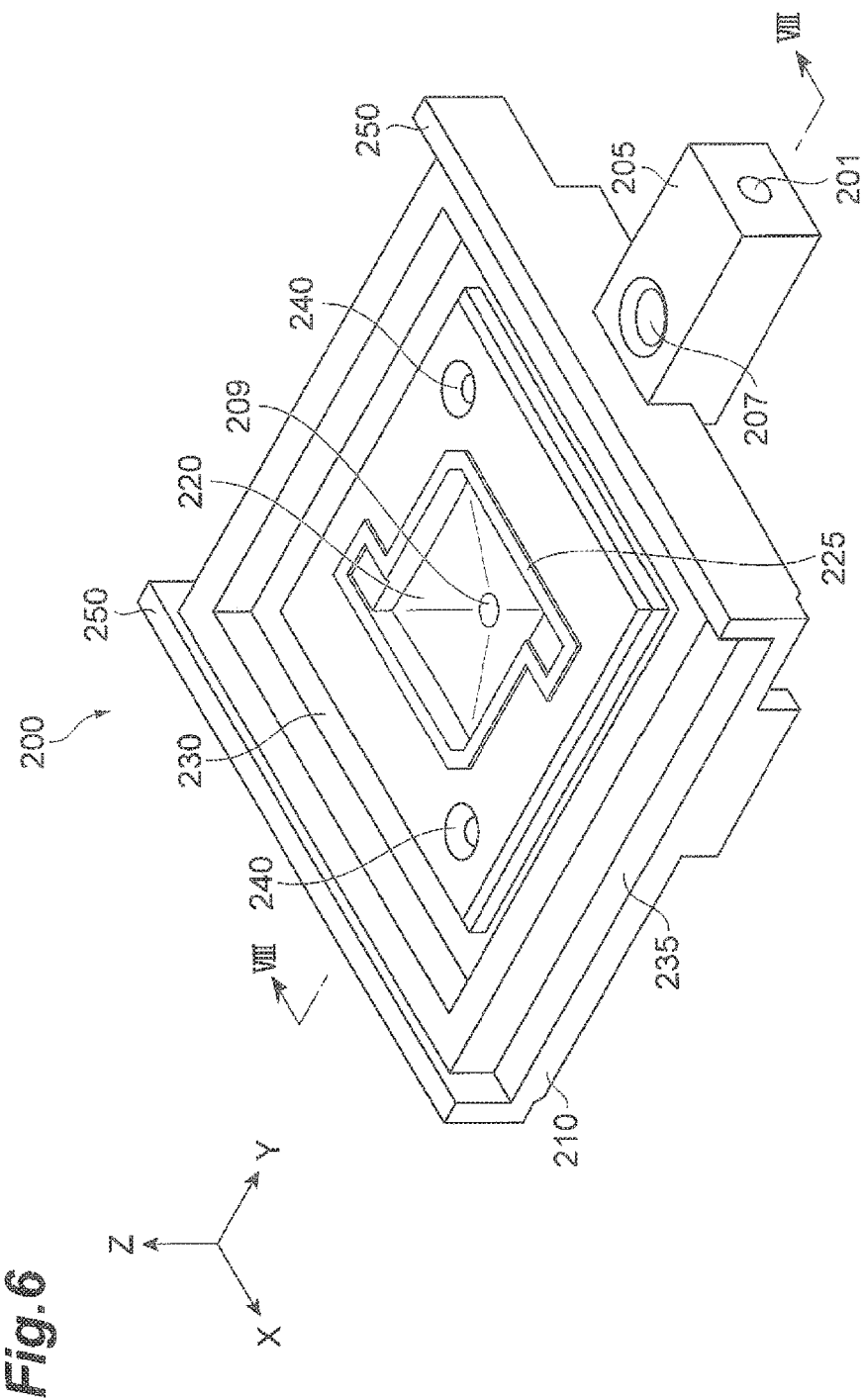
FIG. 6 is a schematic perspective view of the storage member seen from above.
Figure 7:
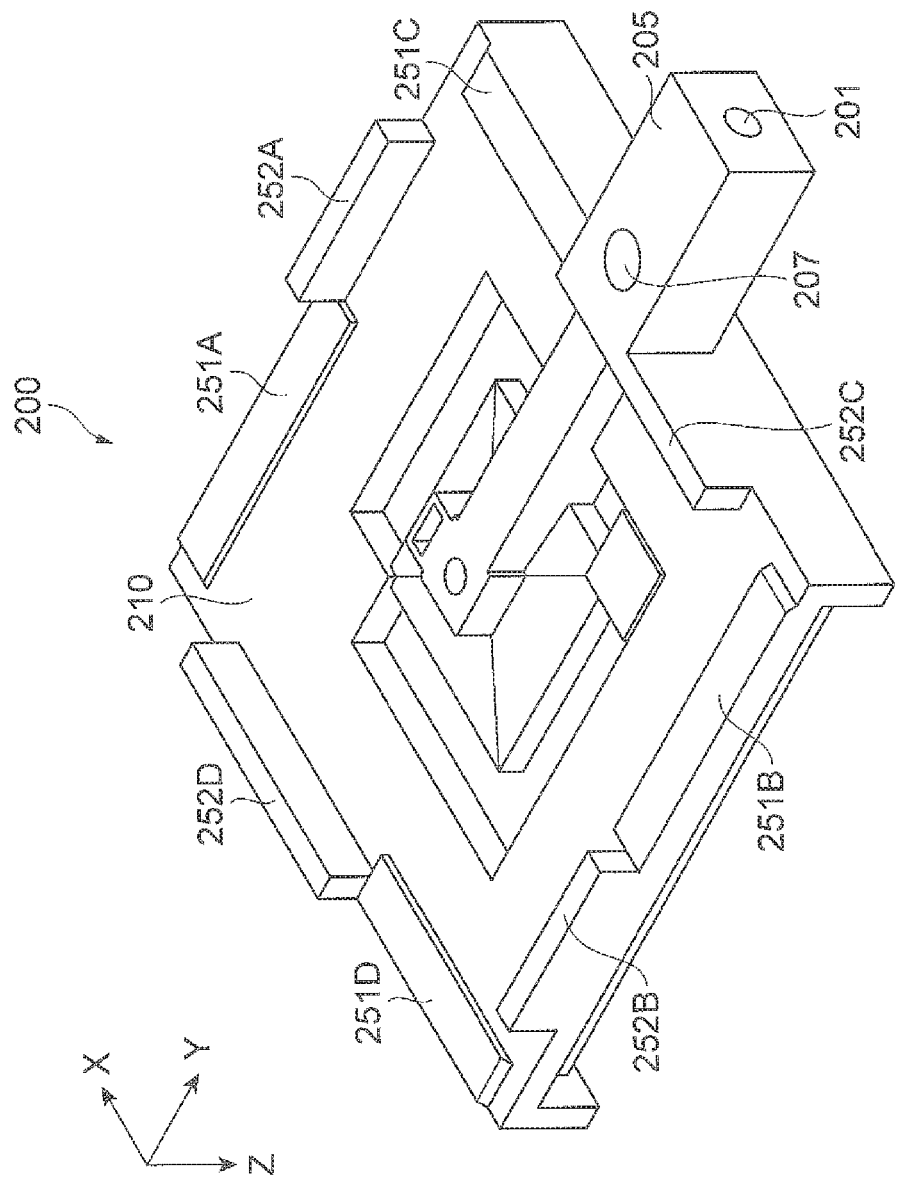
FIG. 7 is a schematic perspective view of a storage member seen from below.
Figure 8:
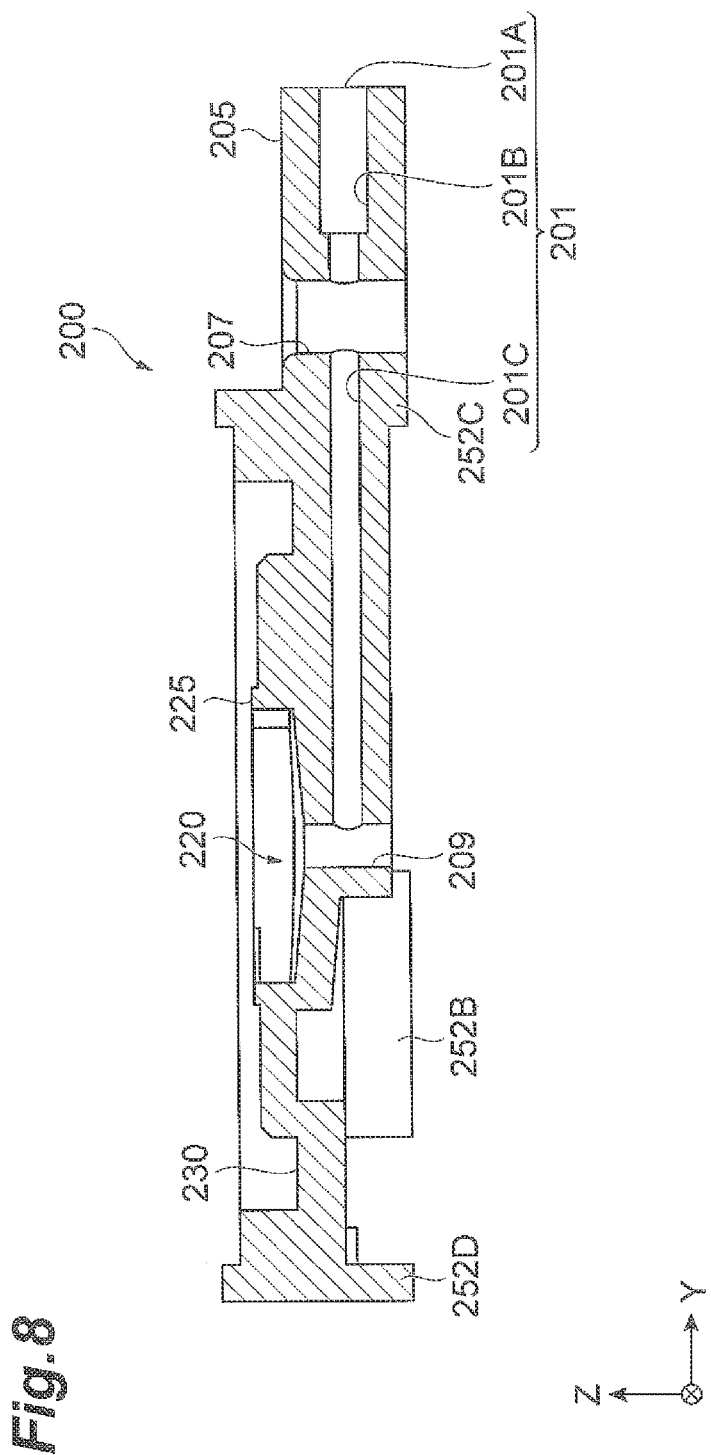
FIG. 8 is a view illustrating the inner structure of the storage member and an arrow view of the VIII-VIII section in FIG. 6.

Subsequently, the storage member 200 will be described. FIGS. 6 to 8 are views illustrating the configuration of the storage member 200. FIG. 6 is a schematic perspective view of the storage member 200 seen from above. FIG. 7 is a schematic perspective view of the storage member 200 seen from below. FIG. 8 is an arrow view of the VIII-VIII section in FIG. 6.

As illustrated in FIGS. 6 to 8, in the storage member 200, a channel part 205 is attached to a main body part 210 made of a plate member having an approximately square shape so as to protrude along the Y axis direction from a side edge of the main body part 210 to the outside. The channel part 205 is attached to the center of the side edge of the main body part 210.

The storage member 200 is provided with a discharge region 220 made of a concave space where the test liquid passing through the filter passes. The discharge region 220 is provided at the lower position of the region attaching the filter so that the region where the through-hole is provided in the filter attached to the storage member 200 is included when the cell trapping device 1 is seen from above. The discharge region 220 is connected to the discharge channel 201 through a perforation 209 for connection and is a space for discharging the test liquid through the discharge channel 201.

The discharge channel 201 will be further described using FIG. 8. In the inside of the channel part 205, the discharge channel 201 extending along the Y axis is provided. The discharge channel 201 is configured to include a discharge opening 201A, a channel 201B extending from the discharge opening 201A to the inside, and a channel 201C connecting to the channel 201B and having a smaller hole diameter than the bore diameter of the channel 201B. A perforation 207 passing through the channel part 205 in the vertical direction (the Z axis direction) is provided on the channel 201C. In the perforation 207, a valve provided with a perforation functioning as a channel opening and closing valve is inserted. This allows the opening and closing of the channel 201C to be carried out by this valve. A perforation 209 for connecting the discharge region 220 and the discharge channel 201 is provided at the edge part of the discharge channel 201 in the main body part 210 side so as to communicate to the discharge channel 201. This allows the liquid (the test liquid or the treatment liquid) reached to the discharge region 220 through the filter to be transferred to the discharge opening 201A through the perforation 209, the channel 201C, and the channel 201B.

At the peripheral edge of the discharge region 220, a second protrusion part 225 for reducing fluctuation of the height of the filter in the XY plane to planarize is provided so as to extend from the main body part 210 toward the upper position. As illustrated in FIG. 6, when the storage member 200 is seen from above, the second protrusion part 225 has an approximately quadrilateral shape in XY plane and has a shape like a two-blade wind turbine. This shape corresponds to the first protrusion part 125 of the lid member 100. Here, an excessively narrow width of the contact surface of the second protrusion part 225 and the filter 30 described below results in an insufficient plane, whereas an excessively wide width results in no liquid sealing effect due to excessively low surface pressure. Consequently, the width of the second protrusion part 225 is preferably 0.1 mm to 3 mm and more preferably 0.5 mm to 2 mm. The high height of the second protrusion part 225 can increase the pressure at the time of sandwiching the filter and thus the seepage prevention effect of the liquid can be further improved. However, the excessively high height of the protrusion part results in increase in the thickness of the whole cell trapping device 1. This may cause trouble in observation operation of the cell trapping device and thus the thickness is preferably 0.05 mm to 1 mm and more preferably 0.1 mm to 0.8 mm.

A second fitting part 230 made of a concave part having a quadrilateral shape is formed so that the second fitting part 230 is provided away from the second protrusion part 225 and surrounds the peripheral edge of the second protrusion part 225. The second fitting part 230 is provided so as to correspond to the first fitting part 130 of the lid member 100. From the viewpoint of the capacity of the first fitting part 130, the length of the one side of the second fitting part 230 in the X axis direction or the Y axis direction is required to be longer than the length of the fitting part 130 and is preferably 9 mm to 31 mm, more preferably 16 mm to 26 mm, and further preferably 16 mm to 21 mm. The width of the concave part configuring each side of the second fitting part 230 is preferably 1.1 mm to 6 mm, more preferably 1.1 mm to 4 mm, and further preferably 1.6 mm to 3 mm. In the present embodiment, the example in which the first fitting part 130 is the convex part and the second fitting part 230 is the concave part is described. However, these parts may have the opposite configurations.

A region located between the second protrusion part 225 and the second fitting part 230 and not providing a part corresponding to the blade in the "shape like a two-blade wind turbine" is provided with two bottomed holes (hole parts) 240 in diagonal positions with each other. The bottomed holes 240 are used for aligning the storage member 200 and the filter 30 as described below. The bottomed holes 240 may be through-holes passing through the storage member. In the present embodiment, the example in which the bottomed holes 240 are provided in the storage member 200 side is described. However, the bottomed holes 240 may be provided at the lid member 100 side.

The difference of dimensions between the second fitting part 230 of the storage member 200 and the first fitting part 130 of the lid member 100 is preferably determined in consideration of the thickness of the filter 30. The difference between the inside of the second fitting part 230 and the inside of the first fitting part 130 (the difference of the insides of the fitting part seen from the center of the member) is preferably 0.005 mm to 0.3 mm, more preferably 0.005 mm to 0.2 mm, and further preferably 0.005 mm to 0.1 mm. When the difference between the inside of the second fitting part 230 and the inside of the first fitting part 130 is thinner than the thickness of the filter, the gap is thinner than the thickness of the filter. However, if the lid member and the storage member are made of plastics, the lid member and the storage member relatively have elasticity and fixing force when the filter is fitted is increased and thus this configuration is preferable.

In the storage member 200, in addition to the second fitting part 230, alignment grooves 235 are provided only in the direction orthogonal to the direction extending to the outer edge providing the channel part 205 in the outer edges of the main body part 210 (the X axis direction), that is, the side extending along to the Y axis direction. These alignment grooves 235 are used for aligning and orienting the lid member 100 and the storage member 200 at the time of assembling the cell trapping device 1. In the same direction as the direction where the outer edge providing the channel part 205 in the outer edges of the main body part 210 extends (the X axis direction), covering parts 250 extending toward the upper position and covering the side parts of the lid member 100 are provided.

As illustrated in FIG. 7, in the main body part 210 having the approximately square shape, a storage member side guide parts 251 (251A to 251D) extending along peripheral edge parts from respective ends (respective corners) as a starting point are provided at the four-side peripheral edge part of the surface to be a lower surface (a surface exposed to the outside) at the time of assembly. The storage member side guide parts 251A to 251D are protrusions protruding toward the lower position (toward the upper position in FIG. 7) of the storage member 200 and defines a direction where the fastening members 60 slide by engaging the claws of the fastening members 60 described below with the storage member side guide parts. The storage member side guide parts 251A to 251D are provided at positions corresponding to the lid member side guide parts 151A to 151D, respectively, in the thickness direction of the housing 10 at the time of assembling the storage member 200 and the lid member 100. For example, in the peripheral edge part attaching the channel part 205, the storage member side guide part 251C is provided at the side being the right side illustrated in FIG. 7 when the channel part 205 is seen from the Y axis direction as the front side with respect to the main body part 210 in FIG. 7. As illustrated in FIG. 7, stepped parts of the starting points of the storage member side guide parts 251A to 251D and the upper surface of the main body part 210 are chamfered obliquely.

The storage member side guide parts 251 (251A to 251D) are extended from the position close to the edge part of the main body part 210 as the starting points to an approximately center part in each peripheral edge part of the main body part 210. From the approximately center part, storage member side stoppers 252 (252A to 252D) are continuously provided and continuously extend along the peripheral parts. The storage member side stoppers 252A to 252D are protrusions having higher height than the height of the storage member side guide parts 251A to 251D, define limit positions where the fastening members 60 described below slide along the storage member side guide parts 251A to 251D, and function as the legs of the cell trapping device 1 at the time of use and observation of the cell trapping device 1 (refer to FIG. 8). The storage member side stoppers 252A to 252D extend to the positions close to the edge parts opposite to the starting points of the storage member side guide parts 252A to 252D in each peripheral edge part. The storage member side stopper 252C in the peripheral edge part attaching the channel part 205 is integrated with the base parts of the channel parts 205.

When the lid member 100 and the storage member 200 are made of plastics such as an acrylic resin, these members can be produced by injection molding. The method for producing the lid member 100 and the storage member 200, however, is not limited to the method for production described above.

(Fastening Member)

Subsequently, the fastening member 60 will be described. The FIG. 9(A) is a perspective view of the fastening member 60 and FIG. 9(B) is a front view of the fastening member 60. The fastening member 60 is an integratedly molded member forming a shape in which a transverse section is one face of the side part of the tubular body being an approximately quadrilateral shape (that is, a U shape of the transverse section) and fastens the lid member 100 and the storage member 200 by clamping so as to press from both sides in a direction where these members are overlapped (a direction intersecting with the filter).

At the inner surface of the U shape and a tip part of the U shape, the fastening member 60 has claws 61 and 61 protruding each other in opposite directions where the lid member 100 and the storage member 200 should be clamped. These claws 61 and 61 extend to a direction corresponding to the height of the "tubular body of the approximately quadrilateral shape". In other words, the claws 61 and 61 extend to a direction along the peripheral edge parts of the lid member 100 and the storage member 200 when the fastening members 60 are located at the peripheral edge part of the housing 10 and can slide along the lid member side guide parts 151 and the storage member side guide parts 251 by engaging with the lid member side guide parts 151 and the storage member side guide parts 251. From the viewpoint of more uniformly pressing, the length of the fastening member 60 in the sliding direction is preferably 3 mm to 20 mm, more preferably 4 mm to 15 mm, and further preferably 5 mm to 10 mm. With respect to the length of fastening member 60 in the sliding direction, a ratio of the length of fastening member 60 in the sliding direction to the length of the one side of the peripheral edge part of the housing 10 equipped with the fastening member 60 is preferably 0.2 to 0.4.

From the viewpoint of uniformly pressing the peripheral edge part of the housing 10 to fasten, identical fastening members are preferably used as the fastening members 60. For example, the fastening members 60 having the same shape and the same size or having less fluctuation of the applied pressure are preferably used.

As the material for the fastening member 60, a material having appropriate elasticity (2 GPa to 5 GPa as Young's modulus), excellent tensile strength (500 kg/cm$^2$ or more), and elongation in a range of 10% to 100% is preferable and a polycarbonate resin or a polyacetal resin is preferable.

(Filter)

Subsequently, the filter 30 provided between the lid member 100 and the storage member 200 will be described using FIG. 10.

Figure 10:
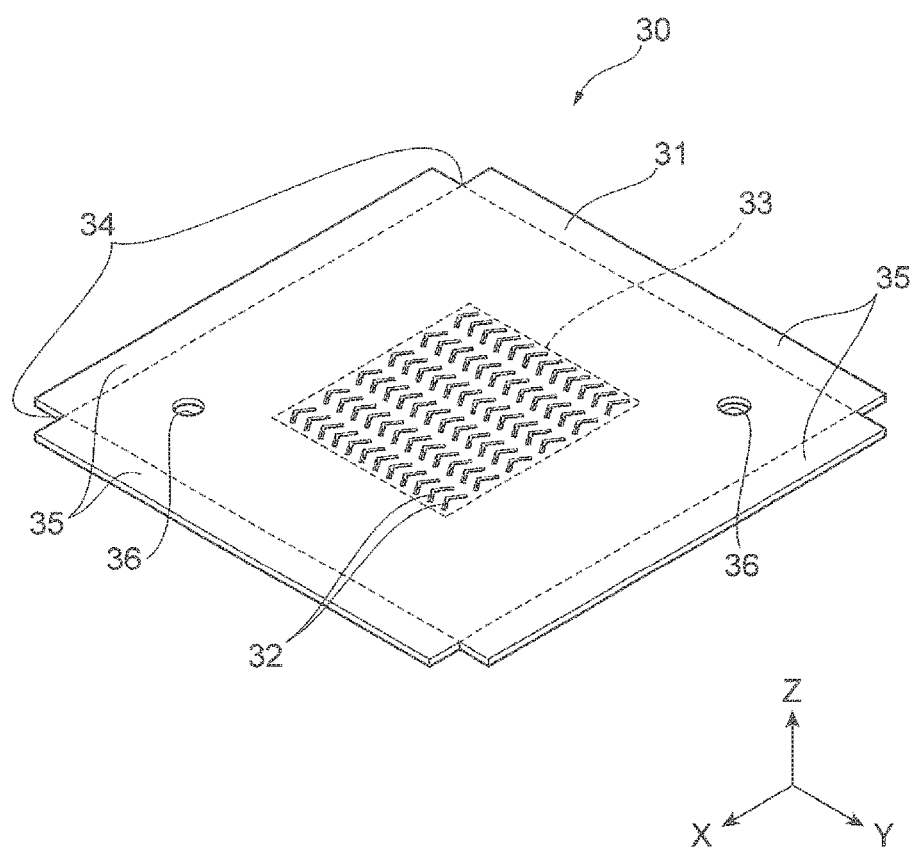
FIG. 10 is a view illustrating the structure of a filter.

As illustrated in FIG. 10, the filter 30 is configured to include a filter region 33 forming a plurality of through-holes 32 in a sheet 31 in a thickness direction to pass the test liquid. In FIG. 10, the shape of the through-holes 32 in the surface of the sheet 31 is a wave-like shape. The through-holes 32 having the wave-like shape is formed by connecting a plurality of perforations having a rectangular shape or a rounded rectangular shape in the surface of the sheet at the edges with each other in a predetermined intersection angle. In the filter 30 of FIG. 10, the wave-like shape of the through-holes 32 is formed along the X axis direction.

The sheet 31 is an approximately square shape and provides cutout parts 34 at four corners. Outside from the region where the cutout parts 34 are formed, folding regions 35 are formed. At the positions outside from the filter region 33 and inside form the outer edge of the filter 30, alignment holes 36 that are through-holes different from the through-holes 32 in the filter region 33 are formed. Two alignment holes 36 are formed at the diagonal positions in the approximately square shape of the sheet 31. The folding regions 35 and the alignment holes 36 are used at the time of attaching the filter 30 to the cell trapping device 1. This will be described below.

The material of the sheet 31 is preferably a metal as a main component. The main component means a component having the highest ratio in the material forming the sheet 31. By using the metal as the main component of the material of the sheet of the filter 30, the fluctuation of the size of the through-holes becomes smaller and thus cells can be separated and concentrated in high accuracy. In addition, metal are more rigid than any other materials such as plastics and thus a size or a shape tends to be retained even when force is externally applied. Therefore, it is considered that separation and concentration in high accuracy are possible by deforming the blood components (in particular, white blood cells) having slightly larger size than the hole diameter of the through-hole to pass through the through-hole. In white blood cells, some white blood cells having almost same size as the target cells to be separated and concentrated exist and thus only the target cells may fail to be distinguished in high concentration simply by the size difference. However, white blood cells has higher deformation capacity than that of the cells and thus white blood cells can pass through the holes smaller than the white blood cells themselves by external force such as suction or pressurization. This may allow the cells and white blood cells to be separated or the cells to be concentrated. Here, the "concentration" means that an existence ratio of the number of the cells that are the target for separation and concentration to the number of the white cells before and after passing the test liquid through the cell trapping device is increased.

Examples of the material of the metal used for the sheet 31 may include gold, silver, copper, aluminum, tungsten, nickel, chromium, and alloys of these metals. The material of the metal, however, is not limited to these metals. The metal may be used singly or may be used as an alloy with other metals or the oxide of the metal for adding functionality. From the viewpoint of price and easy availability, nickel, copper, gold, and a metal containing these metals as a main component are preferably used. In particular, a metal containing nickel as a main component is preferably used. When the sheet 31 is formed of the material containing nickel as the main component, the surface of the nickel is preferably plated with gold. The gold plating can prevent oxidation of the filter surface and thus adhesion of the cells and the blood cell components to filter become uniform. This allows the repeatability of data to be improved.

The thickness of the filter 30 is preferably 3 μm to 100 μm. When the film thickness is determined to be the above range, the filter is easily handled and is adequate for high-precision processing. The height difference of the plane of the filter region in the filter is preferably 16 μm or less, where the height difference is determined as the difference between the maximum and the minimum in focal distances at the time of observing the five places in total of the ends and the center parts of the filter surfaces with a microscope.

The size of the filter 30 depends on the size of the cell trapping device 1. The size of the filter region 33 in the filter 30 provided with the through-holes 32 and passing the test liquid is preferably 25 mm$^2$ to 1,000 mm$^2$. The size is more preferably 25 mm$^2$ to 225 mm$^2$ and further preferably 25 mm$^2$ to 100 mm$^2$. The size of the filter region 33 more than 1,000 mm$^2$ results in increase in a dead space. The size of the filter region 33 less than 25 mm$^2$ results in longer process time. The size of the filter region 33 corresponds to the center part in the introduction region 120 of the lid member 100 illustrated in FIG. 4 and the center part in the discharge region 220 of the storage member 200 illustrated in FIG. 6. In other words, the filter region 33 in the filter 30 is attached to the position corresponding to the center parts described above.

Subsequently, as illustrated in FIG. 10, the shape of the through-holes 32 provided in the filter 30 can be the wave-like shape, that is, a connected through-holes formed by connecting edge parts of two single through-holes having a rectangular shape or a rounded rectangular shape (a rectangular shape whose edge corners are rounded) in a predetermined angle. For the through-hole having the rectangular shape or the rounded rectangular shape (hereinafter, collectively called an "approximately rectangular shape"), the length of the shorter side of the approximately rectangular shape of the single through-hole can be set in a range of about 5 μm to about 15 μm. On the other hand, the length of the longer side can be adequately changed depending on the size of the filter and the range is about 10 μm to 5 mm. The hole diameter of the through-holes 32 provided in the filter 30 can be changed depending on the size of the trap-target cells. The hole diameter of the through-holes means a diameter of the largest sphere that can pass through each through-hole 32. For example, the hole diameter of the through-holes 32 in FIG. 10 can be the shorter side of the single through-hole.

For the shape of the through-holes 32, the case of the wave-like shape is described in FIG. 10 and this shape can be changed to the other shapes. As illustrated in FIG. 11, representative example of the modified shapes of the through-hole may include (A) a circular shape, (B) a rectangular shape, (C) a round rectangular shape (edge corners are rounded), (D) a round rectangular shape (shorter sides of the rectangular shape is arcs), (E) a wave like shape (three rounded rectangular shapes are continuously connected so that the edges of the single through-holes having the rectangular shape are alternately faced with each other), and (F) a circular wave-like shape (five semicircle grooves are connected at the edges alternately facing with each other). The shape of the through-hole is not particularly limited to the examples illustrated in FIG. 11. For example, the shape may be a wave-like shape in which four or more of the single holes of the round rectangular shape are connected or may be a continuous through-hole shape in which a plurality of single through-holes having not the round rectangular shape but the rectangular shape whose corners are not rounded are connected.

Example of a method for production the filter in which through-holes 32 having a small hole diameter in the filter 30 can be precisely formed may include a method of using metal plating using a photoresist. Specifically, the method for producing includes the steps of laminating a photoresist on a metal foil; overlapping a photomask having a translucent part similar to a shape of a through-hole on the photoresist to expose; forming a photoresist pattern by developing the exposed photoresist and removing an uncured part of the photoresist; plating the removed part of the photoresist pattern with a metal to form a metal plating pattern having lower height than the height of the photoresist pattern; removing the metal foil by chemical dissolution to give a structure made of the metal plating pattern and the photoresist pattern; and removing the photoresist pattern from the structure to give a metal plating pattern (filter) having the through-holes 32 corresponding to the translucent part. The method for producing the filter 30, however, is not limited to the above method.

(Method for Assembling Cell Trapping Device)

Figure 12:
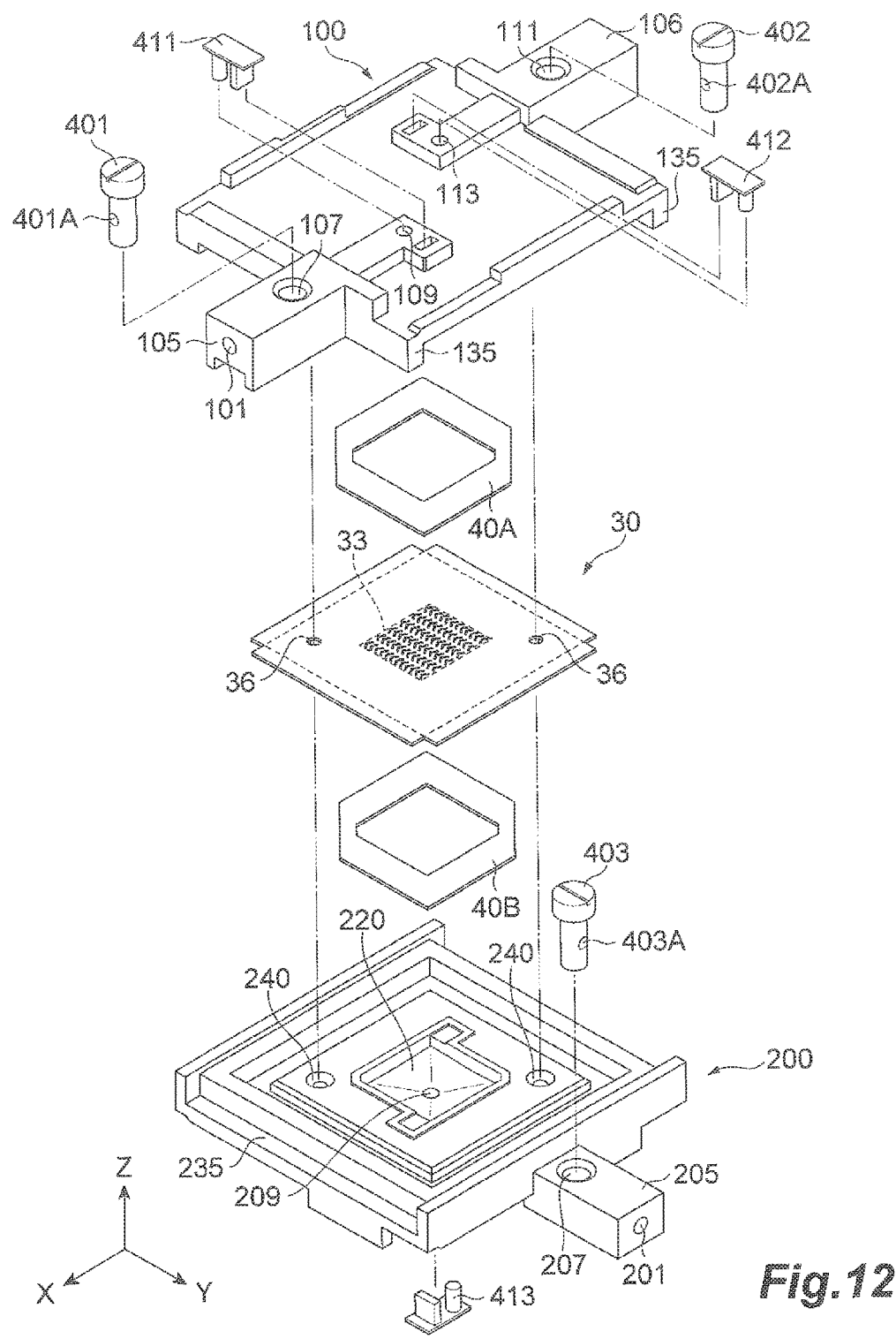
FIG. 12 is a disassembled perspective view illustrating the configuration of the cell trapping device.
Figure 13:
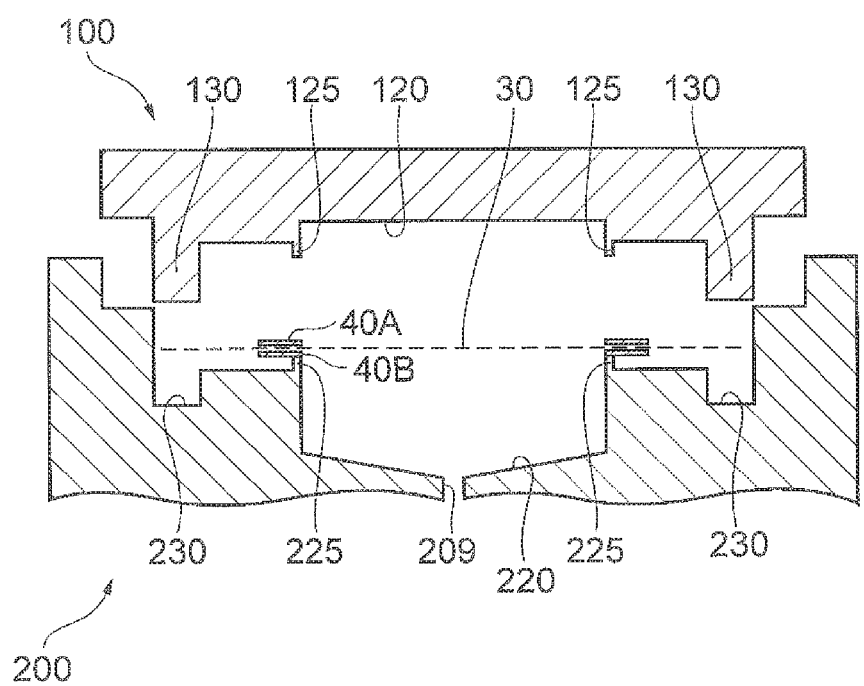
FIG. 13 is a view schematically illustrating the section before the lid member, the filter, a gasket, and the storage member are assembled and corresponds to the sectional view of the XIII-XIII section of FIG. 1.
Figure 14:
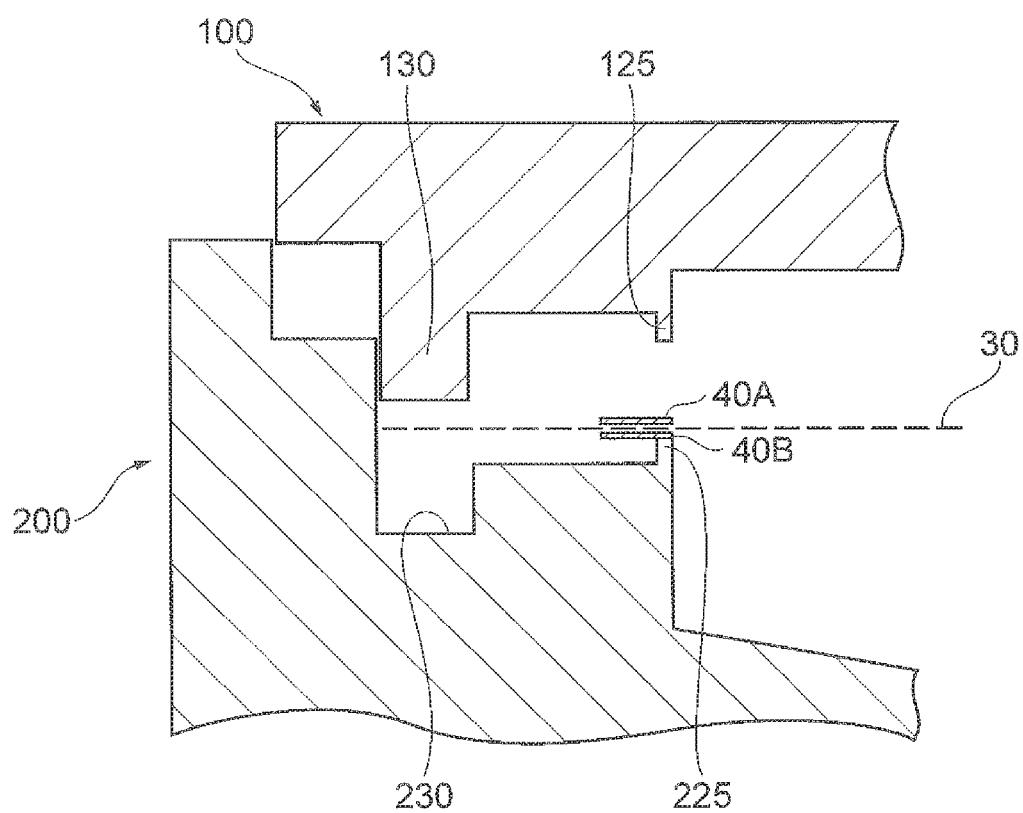
FIG. 14 is a view in which only the left part in FIG. 13 is enlarged.
Figure 15:
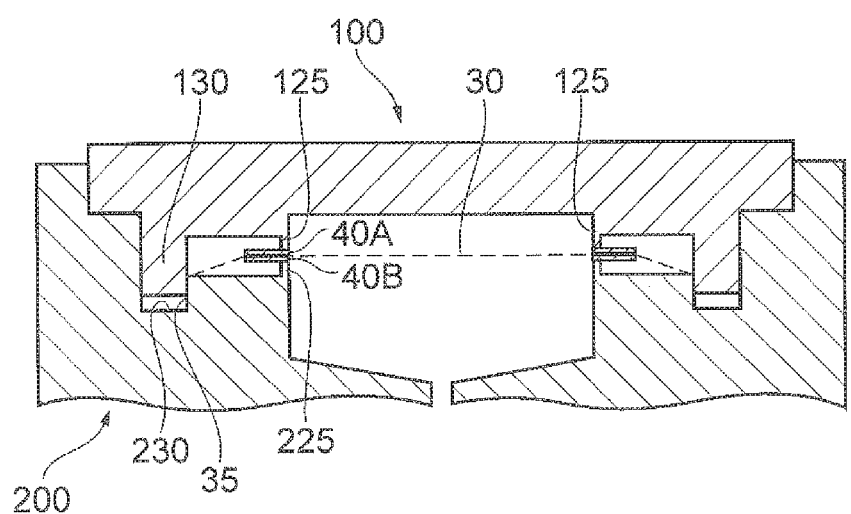
FIG. 15 is a view after the lid member, the filter, the gasket, and the storage member are assembled and the view corresponds to FIG. 13.
Figure 16:
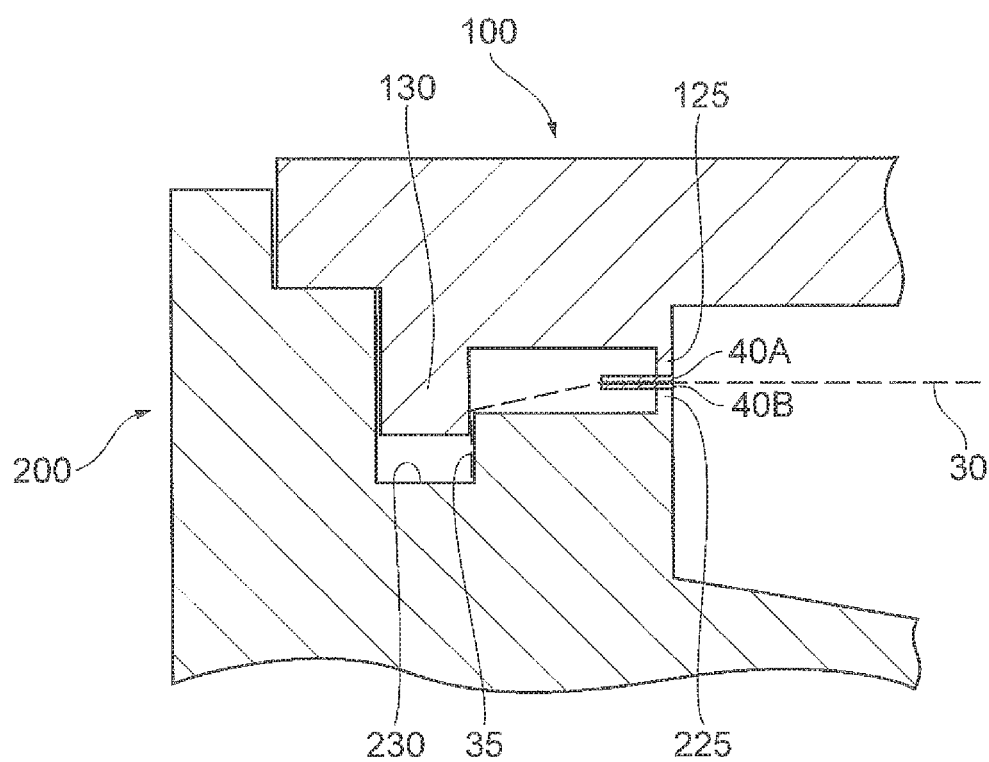
FIG. 16 is a view in which only the left part in FIG. 15 is enlarged and the view corresponds to FIG. 14.
Figure 17:
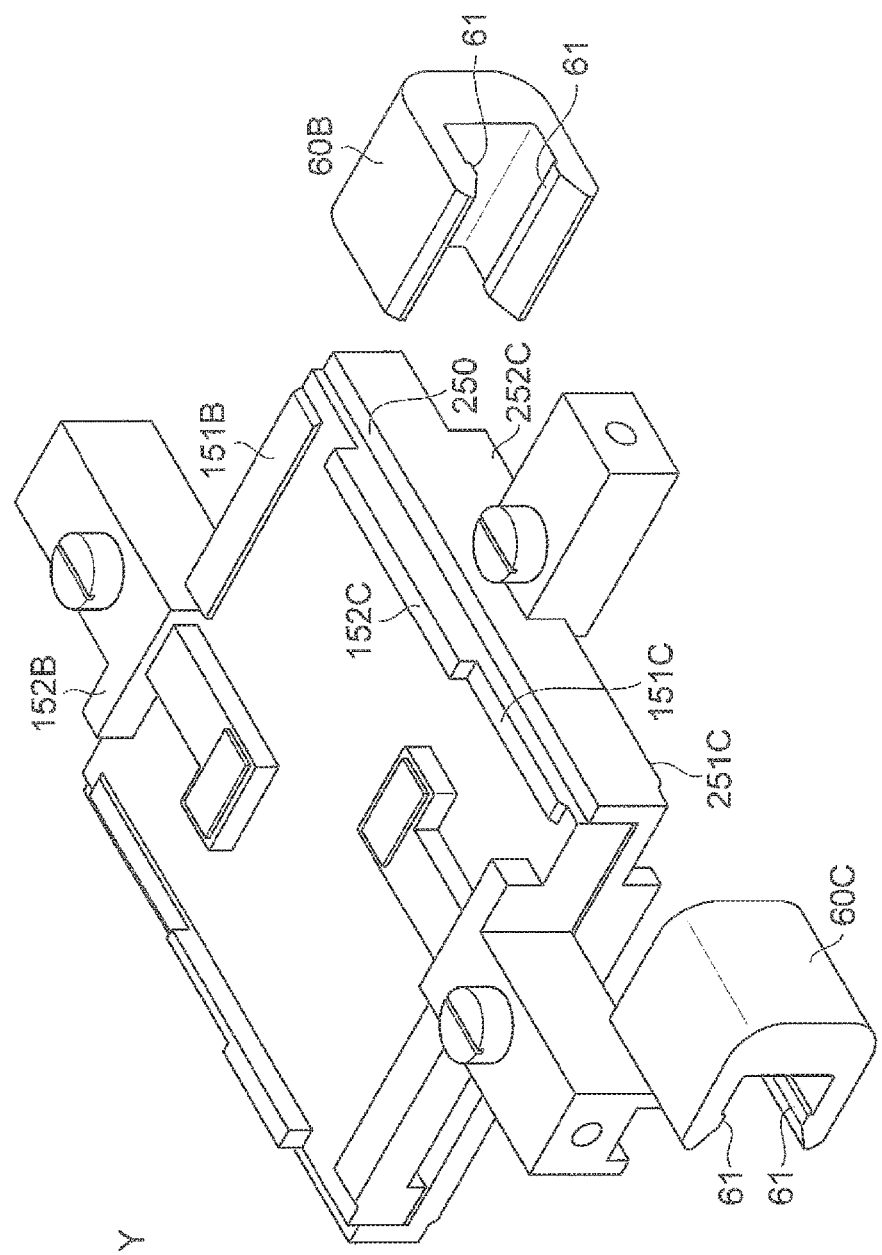
FIG. 17 is a view illustrating a method for equipping the fastening members.

Subsequently, the method for assembling cell trapping device 1 will be described using FIG. 12 to FIG. 17. FIG. 12 is a disassembled perspective view illustrating the configuration of the cell trapping device 1. FIG. 13 is a view schematically illustrating the section before the lid member 100, the filter 30, sealing members (gaskets) 40, and the storage member 200 are assembled and corresponds to the sectional view of the XIII-XIII section of FIG. 1. FIG. 14 is a view in which only the left part in FIG. 13 is enlarged. FIG. 15 is a view after the lid member 100, the filter 30, the sealing member 40, and the storage member 200 are assembled and the view corresponds to FIG. 13. FIG. 16 is a view in which only the left part in FIG. 15 is enlarged and the view corresponds to FIG. 14. FIG. 17 is a view illustrating a method for equipping the fastening members.

As an outline of the method for assembling the cell trapping device 1, as illustrated in FIG. 12 to FIG. 14, the storage member 200, the sealing member 40B, the filter 30, the sealing member 40A, and the lid member 100 are stacked in this order and thereafter, as illustrated in FIG. 15 and FIG. 16, the storage member 200 and the lid member 100 are fitted. By equipping the fastening members 60 to the housing 10 formed by fitting the lid member 100 and the storage member 200, the lid member 100 and the storage member 200 are fastened each other and the assembly of the cell trapping device 1 is completed.

First, as illustrated in FIG. 12, the cell trapping device 1 is assembled by stacking the lid member 100, the lid member side sealing member 40A, the filter 30, the storage member side sealing member 40B, and the storage member 200 in this order from upward to downward along the Z axis. At this time, the channel parts 105 and 106 of the lid member 100 are determined to extend along the X axis direction and the channel part 205 of the storage member 200 is determined to extend along the Y axis direction by setting the lid member 100 and the storage member 200 in a direction where the pair of the alignment protrusion parts 135 and the alignment grooves 235 are faced. This provides a configuration in which the channel parts 105, 106, and 205 protrude in different directions with each other.

The sealing members 40 (40A and 40B) are members sandwiched between the first protrusion part 125 of the lid member 100 and the filter 30 and the second protrusion part 225 of the storage member 200 and the filter 30. The sealing members 40 are located whole regions where the first protrusion part 125 and the second protrusion part 225 exist and have an annular shape formed by punching out the center as the shape of the filter region 33 in order not to cover the filter region 33. The material of the sealing members 40 is not particularly limited as long as the material has elasticity and can maintain liquid-tight properties of the housing 10. For example, silicone rubber is used. The thickness of the sealing members 40 is preferably 0.05 μm to 0.3 μm.

Valves 401, 402, and 403 that function as channel opening and closing valves are inserted into perforations 107, 111, and 207, respectively, after assembling these members. These valves 401, 402, and 403 are provided with channel holes 401A, 402A, and 403A, respectively, extending in a horizontal direction. When the valves are inserted into the perforations 107, 111, and 207, the channel holes of the valves correspond to the introduction channels 101 and 102 and the discharge channel 201, respectively. By rotating the valves, opening and closing of the channel holes and introduction channels (or discharge channel) can be switched. At the time of use, the leakage of the liquid is prevented and the introduction and discharge of the liquid are guided to appropriate directions by inserting stoppers 411, 412, and 413 into the perforations 109, 113, and 209, respectively.

The configuration of the inside of the cell trapping device 1 when the cell trapping device 1 is assembled using FIG. 13 to FIG. 16 will be described. FIG. 13 is a view schematically illustrating the section before the lid member 100, the filter 30, and the storage member 200 are assembled and corresponds to the sectional view of the XIII-XIII section of FIG. 1. Here, the channel part 205 is not illustrated. FIG. 14 is a view in which only the left part in FIG. 13 is enlarged. FIG. 15 is a view after assembly and FIG. 16 is an enlarged view thereof.

As illustrated in FIG. 12 to FIG. 14, the storage member side sealing member 40B is located at the position being the upper position of the second protrusion part 225 of the storage member 200.

Subsequently, the filter 30 is located at the position being upper position of the discharge region 220, the second protrusion part 225, and the second fitting part 230 of the storage member 200. When the filter 30 is located, the filter 30 can be easily aligned by inserting stick-like jigs into the alignment holes 36 and 36 of the filter 30 and inserting the edge of these jigs into the bottomed holes 240 and 240 of the storage member 200. Alternatively, the filter 30 can be also easily aligned by electing the jigs at the bottomed holes 240 and 240 of the storage member 200 and passing the alignment holes 36 of the filter 30 through the elected jigs. The positions corresponding to the bottomed holes 240 and the alignment holes 36 in the storage member side sealing member 40B are cut out so that the filter 30 can be aligned using the jigs as described above (refer to FIG. 12). By carrying out the alignment as described above, the through-holes of the filter 30 can be easily and always located in the same predetermined direction at the time of assembling the cell trapping device 1 as well as the filter 30 can be located in high accuracy. This results in further improving the repeatability of cell trap.

Subsequently, the lid member side sealing member 40A is located at the position being the upper position of the filter 30. Then, the lid member 100 is located at the position where the first protrusion part 125 and second protrusion part 225 correspond and at the position where the first fitting part 130 and the second fitting part 230 correspond and these members are approached in the vertical direction.

As illustrated in FIGS. 15 and 16, the lid member 100 and the storage member 200 can be approached to the position where each of the first protrusion part 125 and the second protrusion part 225 sandwiches the filter 30 through the lid member side sealing member 40A and the storage member side sealing member 40B. At this time, the first fitting part 130 and the second fitting part 230 stop in a state that a part of the fitting part 130 and a part of the second fitting part 230 are fitted. At this time, the filter 30 is supported by sandwiching the filter with the first protrusion part 125 and the second protrusion part 225 and is sandwiched between the first fitting part 130 and the second fitting part 230 at further outer position. As a result, the folding regions 35 of the filter 30 are folded downward mainly by pressing down the lid member 100. By sandwiching the filter 30 so as to press the filter 30 from the periphery in a direction from the center part of the inside of the filter 30 to the outside, the tensile force from the center to the outside is applied and the filter 30 is sandwiched between the lid member 100 and the storage member 200 in a state of applying the tensile force. This reduces fluctuation of the height of the filter surface and results in the excellent smoothness of the filter 30.

Nonuniform force at the time of sandwiching the filter 30 with the lid member 100 and the storage member 200 may cause strain to generate winkles or slack in the filter 30. Consequently, the second fitting part 230 of the storage member 200 and the first fitting part 130 of the lid member 100 are provided around the entire outer edge circumference of the filter 30 and are preferably fitted so as to uniformly sandwich the filter 30. However, by sandwiching the filter 30 with the first protrusion part 125 and the second protrusion part 225, slight tensile force is applied in the circumferential direction to generate winkle and thus the clearance parts for reducing the winkles are preferably formed by providing the cutout parts 34 at the four corners of the filter 30.

After the storage member 200 and the filter 30 are aligned using the jigs, the jigs are removed before the lid member 100 and the storage member 200 are overlapped. In other words, the filter 30 is aligned to the storage member 200 but the position of the filter 30 is not fixed. Therefore, the filter 30 can respond to position change without physical barrier against the tensile force and the like until the filter 30 is finally fastened in the inside of the housing 10, and thus the winkle and the like are more difficult to generate at the time of fastening the filter 30 between the lid member 100 and the storage member 200.

Subsequently, a method for equipping the fastening members 60 will be described. As illustrated in FIG. 17, the fastening member 60C is approached to the lid member side guide part 151C and the storage member side guide part 251C corresponding to the lid member side guide part 151C from the X axis direction in a state that the U shape opening part faces to the housing 10 side to engage the claws 61 and 61 to the lid member side guide part 151C and the storage member side guide part 251C, respectively. Equipping the fastening member 60C is completed by sliding the fastening member 60C in the X axis direction. At this time, the fastening member 60C may slide until the side part of the fastening member 60C hits the side part of the lid member side stopper 152C and the side part of the storage member side stopper 252C or the slide of the fastening member 60C may stop on the way without hitting the side parts of the stoppers.

Similarly, in order to equip the housing 10 with the fastening member 60B, the fastening member 60B is approached to the lid member side guide part 151B and the storage member side guide part 251B corresponding to the lid member side guide part 151B from the Y axis direction in a state that the U shape opening part faces to the housing 10 side to engage each of the claws 61 and 61 to the lid member side guide part 151B and the storage member side guide part 251B (also refer to FIG. 2). Equipping the fastening member 60B is completed by sliding the fastening member 60B in the Y axis direction. The thickness of the part of the housing 10 that the fastening members 60 clamp, that is, the distance between the outer surfaces of the lid member side guide parts 151 and the storage member side guide parts 251 is larger than the distance between the inner surfaces of the U shape of the fastening member 60. By clamping the part in the housing 10 having thicker distance than the distance of between the inner surfaces of the U shape of the fastening member 60, the filter 30 can be fastened in a state that the filter 30 is evenly stretched. When the sealing members are inserted, the distance between the outer surfaces of the lid member side guide parts 151 and the storage member side guide parts 251 is a distance formed when the storage member 200, the sealing member 40B, the filter 30, the sealing member 40A, and the lid member 100 are overlapped in this order. The difference between the distance between the inner surfaces of the U shape of the fastening member 60 and the distance between the outer surfaces of the lid member side guide parts 151 and the storage member side guide parts 251 is preferably 0 mm to 0.3 mm, more preferably 0.05 mm to 0.25 mm, and further preferably 0.1 mm to 0.2 mm.

When the widths of the lid member side guide parts 151B and 151C are noticed, the width in the X axis direction of the lid member side guide part 151B is larger than the width in the Y axis direction of the lid member side guide part 151C by the thickness of the covering part 250 of the storage member 200. By setting the widths of the lid member side guide part 151B and the lid member side stopper 152B in the X axis direction larger than the widths of the lid member side guide part 151C and the lid member side stopper 152C in the Y axis direction as described above, the distance of the outer edge of the housing 10 and the distance of parts of the lid member side guide parts 151B and 151C where the claws 61 of the fastening members 60 are engaged are equal. In other words, each peripheral edge part of the housing 10 can be equipped with the fastening members 60 having the same shape and the same size. Being able to use the fastening members 60 having the same shape and the same size as described above means being able to use identical fastening members 60 having uniform pressing force. This is preferable from the viewpoint of fastening the housing 10 by pressing the peripheral edge part of the housing 10 in uniform load.

Although not illustrated in FIG. 17, the housing 10 can be equipped with the fastening members 60A and 60D in a similar way as described above. By equipping the housing 10 with the four fastening members 60A to 60D as described above, the fastening members 60 can be located at the peripheral edge part of the housing 10 so as to surround the filter 30.

As illustrated in FIG. 2, in the cell trapping device 1 completed by equipping the housing 10 with the fastening members 60, the length H1 of the housing 10 in the thickness direction (a direction intersecting with the filter) of the fastening member 60 is equal to or less than the thickness 112 of the housing 10. In other words, in the thickness direction of the housing 10, the most protruding part at the outer surface of the storage member 200 (the storage member side stoppers 252A to 252D; also refer to FIG. 8) is more protruding than the edge part of the fastening member 60 in the storage member 200 side and the most protruding part at the outer surface of the lid member 100 (the lid member side stoppers 152A and 152B; also refer to FIG. 5) is more protruding than the edge part of the fastening member 60 in the lid member 100 side. Therefore, for example, when the filter 30 is supported in parallel to the outer surface of the storage member 200 at the time of observing the trapped cells with a microscope without removing the fastening members 60, the observation stage and the filter 30 are maintained in parallel and thus the workability at the time of the microscopic observation is improved (when the edge part of the fastening member 60 in the storage member 200 side is more protruding than the most protruding part at the outer surface of the storage member 200, it is difficult to maintain the observation stage and the filter 30 in parallel). At the time of microscopic observation, the fastening members 60 are not an obstacle of an objective lens in the relative movement of the housing 10 and the objective lens and thus the workability at the time of the observation is improved. In FIG. 2, the top parts of the valves 401 and 402 are more protruded than the lid member side stoppers 152A and 152B. These top parts are sufficiently away from the introduction region 120 of the lid member in such a degree that these top parts are not obstacles for the operation of the objective lens at the time of microscopic observation and thus these top parts are not included in the thickness H2 of the housing 10.

Figure 18:
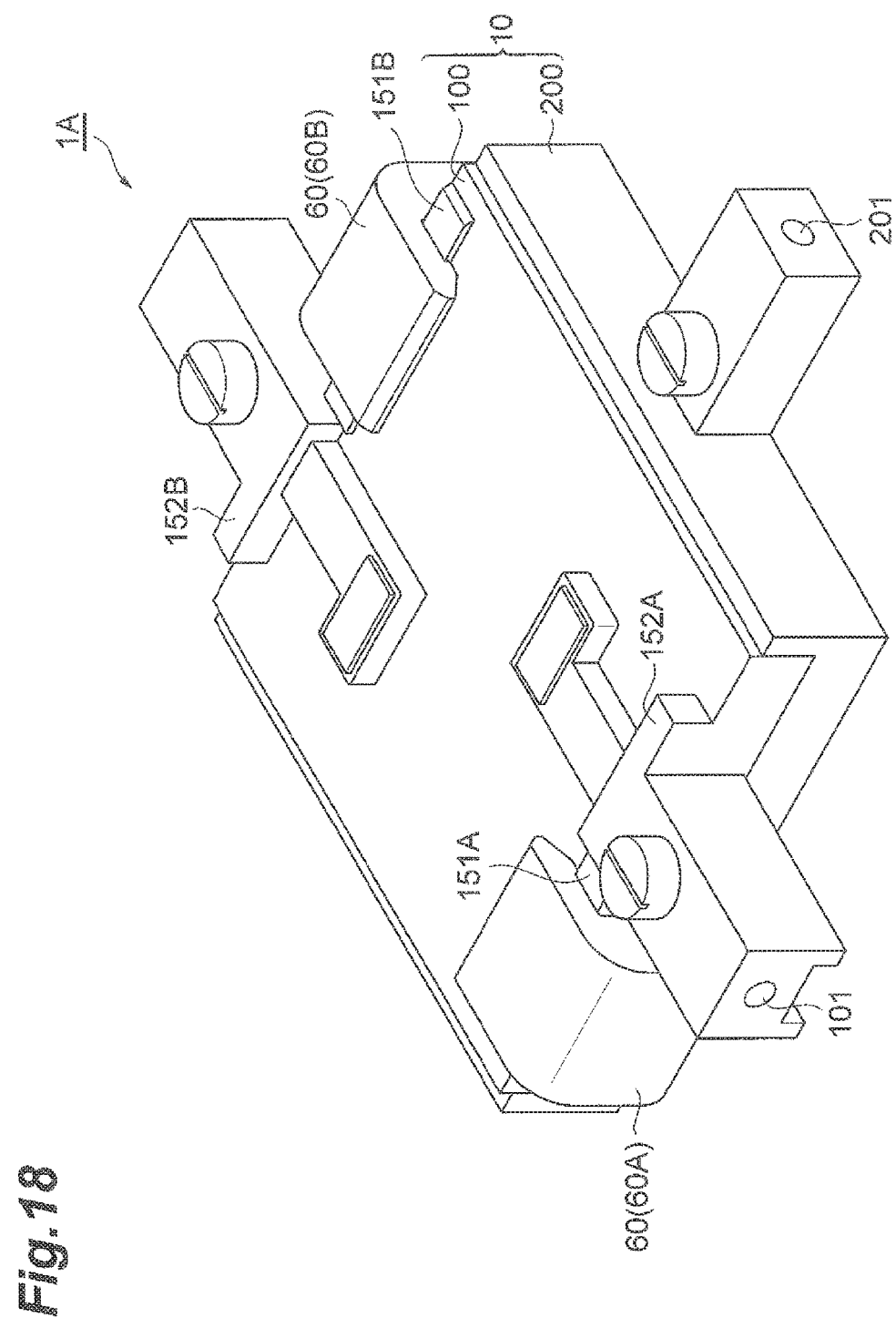
FIG. 18 is a schematic perspective view illustrating the configuration of the modified example of the cell trapping device.

The cell trapping device 1 of the above-described embodiment may be the cell trapping devices of the following embodiments. The cell trapping device 1A illustrated in FIG. 18 is an embodiment in which the device has not four fastening members 60 but two fastening members 60. The cell trapping device 1A is a device in which two fastening members 60C and 60D are removed from the cell trapping device 1. Accordingly, the cell trapping device 1A is configured not to provide the lid member side guide parts 151C and 151D and lid member side stoppers 152C and 152D in the lid member 100 and the storage member side guide parts 251C and 251D and the storage member side stoppers 252C and 252D in the storage member 200. Even in such an embodiment, the repeatability of the support balance of the filter 30 is excellent.

Figure 19:
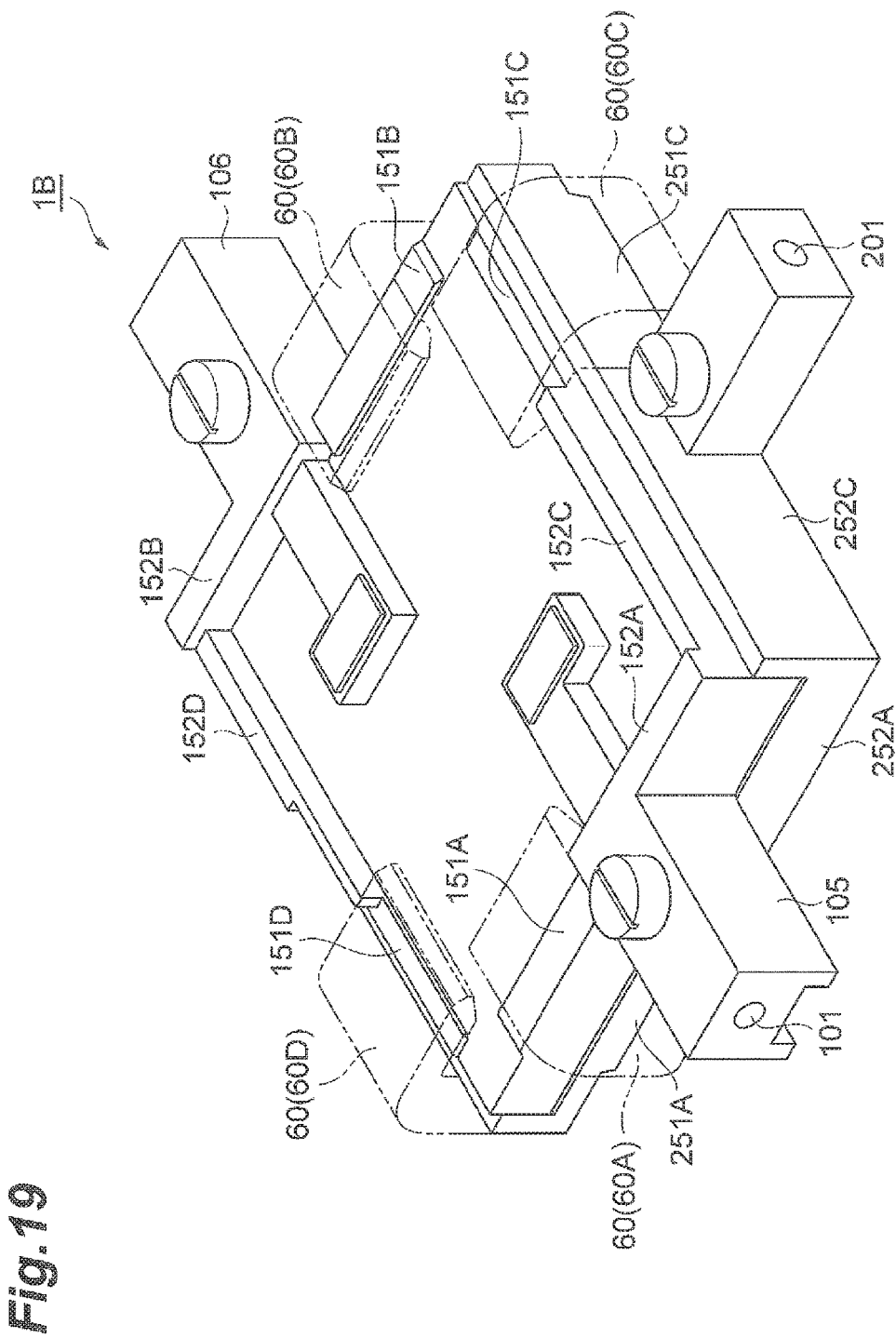
FIG. 19 is a schematic perspective view illustrating the configuration of other modified example of the cell trapping device.

The cell trapping device 1B illustrated in FIG. 19 is an embodiment in which the locations of the guide parts and the stoppers provided in the lid member 100 and the storage member 200 are changed. In two sides of peripheral edge part to which the channel parts 105 and 106 are not attached in the side edges in the four sides of the peripheral edge part of the lid member 100 in the cell trapping device 1B, each pair of the lid member side guide part 151C and the lid member side stopper 152C and the lid member side guide part 151D and the lid member side stopper 152D are located at inverse positions to the cell trapping device 1 illustrated in FIG. 1.

In other words, the lid member side guide part 151C extends along the peripheral edge part from the position close to the corner where the starting point of the lid member side guide part 151B is provided to the side where the channel part 105 is attached. The lid member side stopper 152C is continuously located from the approximately center part of the peripheral edge part and continuously extends along the peripheral edge part. Similarly, the lid member side guide part 151D extends along the peripheral edge part from the position close to the corner where the starting point of the lid member side guide part 151A is provided to the side where the channel part 106 is attached. The lid member side stopper 152D is continuously located from the approximately center part of the peripheral edge part and further extends along the peripheral edge part. Each of the four lid member side stoppers 152 extends to the corner of the lid member 100 and connected to the lid member side stopper 152 in the adjacent side at the corner each other.

Along with the above change in the lid member side guide parts 151 and the lid member side stoppers 152, the storage member side guide parts 251 and the storage member side stoppers 252 of the storage member 200 are also changed in the cell trapping device 1B illustrated in FIG. 19. In other words, the storage member side guide part 251C, the storage member side stopper 252C, the storage member side guide part 251D and the storage member side stopper 252D are provided at the positions corresponding to the lid member side guide part 151C, the lid member side stopper 152C, the lid member side guide part 151D and the lid member side stopper 152D, respectively, in the thickness direction of the housing 10.

In the cell trapping device 1B, the lid member side stopper 152B and the lid member side stopper 152D as well as the lid member side stopper 152A and lid member side stopper 152C are connected to each other at the corners, and thus the lid member 100 obtains higher strength. As a result, deformation caused by the load at the time of clamping by the fastening members 60 becomes smaller and thus the peripheral edge parts of the lid member 100 and the storage member 200 can be pressed by a more uniform load.

Figure 20:
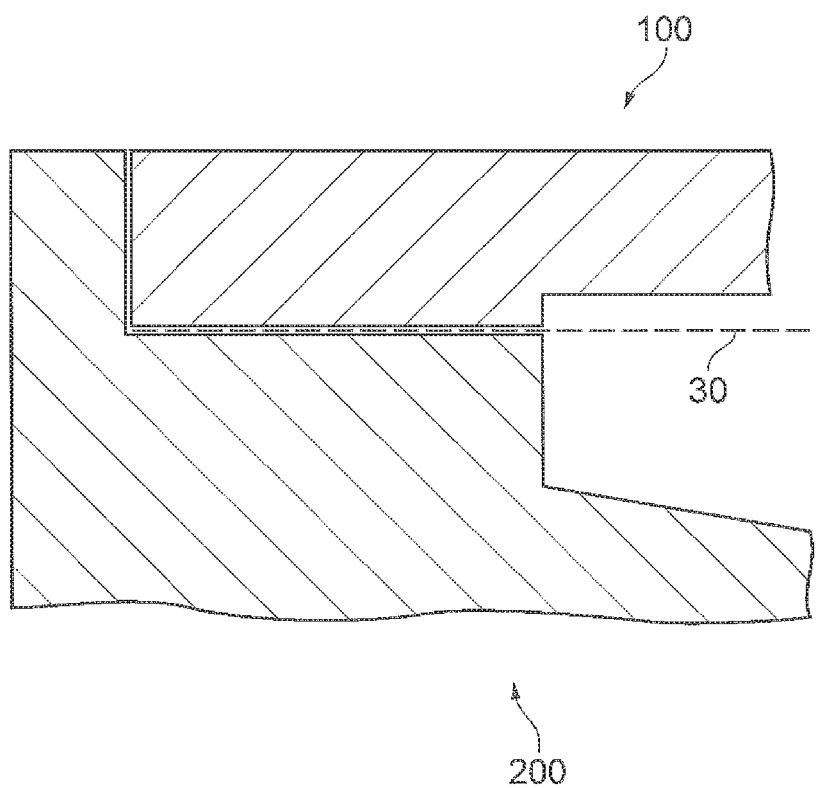
FIG. 20 is a schematic sectional view illustrating the configuration of other modified example of the cell trapping device.

The overlapped part of the lid member 100 and the storage member 200 can also be changed. For example, the first protrusion part 125, the second protrusion part 225, the first fitting part 130, and the second fitting part 230 illustrated in FIG. 16 are not necessarily provided. In this case, as shown in FIG. 20, an embodiment in which, instead of these parts, the overlapped parts of both of the lid member 100 and the storage member 200 are a flat shape to support the filter 30 may be employed. In the embodiment illustrated in FIG. 20, a gasket is not used. An embodiment using a gasket, however, is more preferable because of excellent liquid-tight properties. In this case, the first protrusion part and the second protrusion part illustrated in FIG. 13 are more preferably provided to the lid member 100 and the storage member 200 because of more excellent liquid-tight properties.

Figure 21:
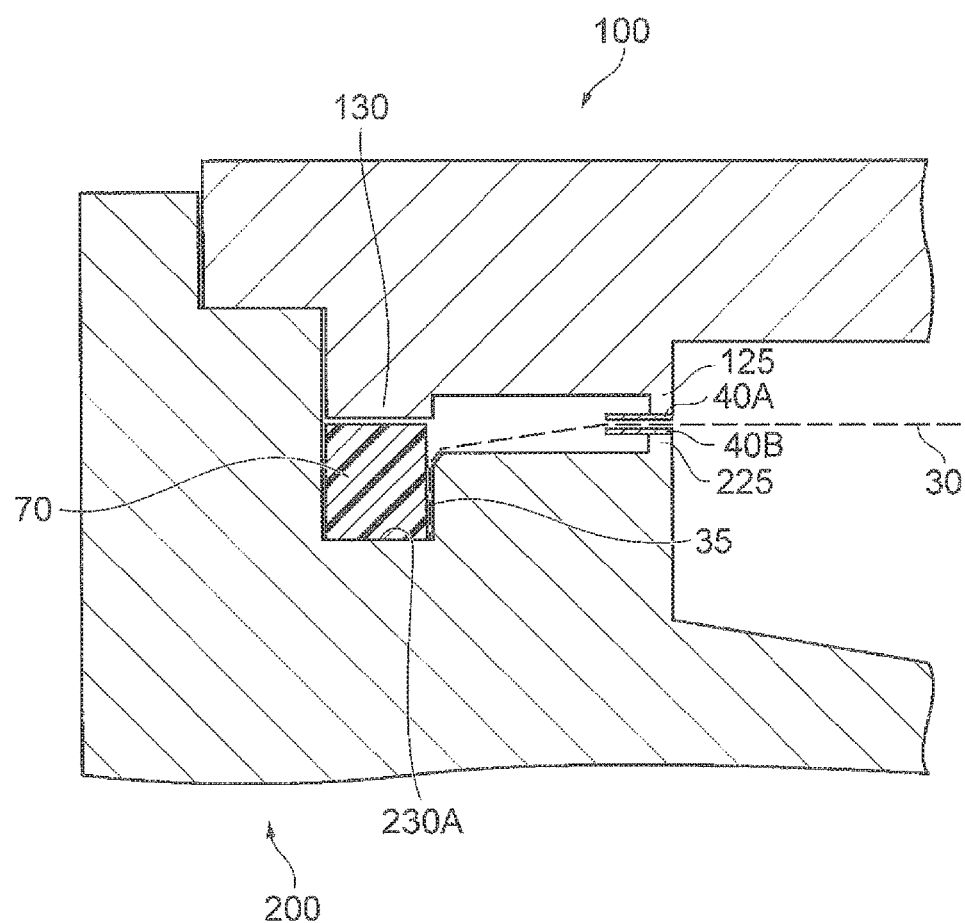
FIG. 21 is a schematic sectional view illustrating the configuration of other modified example of the cell trapping device.

As illustrated in FIG. 21, an embodiment in which the part in which the second fitting part 230 is formed in the cell trapping device 1 is determined as a groove part 230A having a depth in the intersecting direction with the filter 30 and an annular supporting member 70 having a shape that can be accommodated in the groove part 230A is accommodated in the groove part 230A may be employed. Here, compared with the cell trapping device 1 illustrated in FIG. 16, the length of the first fitting part 130 is shortened by the length occupied by the height of the supporting member 70. The supporting member 70 accommodated in the storage member 200 presses the filter 30 to the groove part 230A side of the storage member 200 at the outer circumference side from the filter region 33, whereby the filter 30 is supported.

Here, from the viewpoint of the accommodation capacity for accommodating the first fitting part 130 and the supporting member 70, the dimension of the groove part 230A in the X axis direction or the Y axis direction (a width of the groove) is preferably 1.1 mm to 6 mm, more preferably 1.1 mm to 4 mm, and further preferably 1.6 mm to 3 mm. The dimension of the supporting member 70 in the X axis direction or the Y axis direction (the width of the part constituting one side) may be a dimension that can be accommodated in the groove part 230A. From the viewpoint of fastening the filter 30 by repulsive force using elasticity of the supporting member 70 and the first fitting part 130, however, the supporting member 70 and the groove part 230A preferably have the same dimension or the supporting member 70 is preferably slightly larger than the groove part 230A. Specifically, the difference of the dimensions between the supporting member 70 and the groove part 230A is preferably 0 mm to 0.20 mm and more preferably 0 mm to 0.15 mm, and further preferably 0 mm to 0.10 mm. The thickness of the supporting member 70 (the length of the groove part 230A in the depth direction) is preferably 0.5 mm to 2.0 mm and more preferably 1.0 mm to 1.5 mm.

In this embodiment, not depending on the fitting of the lid member 100 and the storage member 200, the support of the filter 30 is maintained in the state that the filter 30 is still sandwiched between the supporting member 70 and the groove part 230A even when the lid member 100 opens. This further reduces the movement of the filter 30 at the time of disassembly of the housing 10 and thus the risk of the scatter of the trapped cells in the filter 30 is further reduced. The second fitting part 230 of the cell trapping device 1 illustrated in FIG. 1 and FIG. 16 is a quadrilateral shape surrounding the peripheral edge of the second protrusion part 225 (that is, an annular shape). However, the groove part 230A in this embodiment illustrated in FIG. 21 is not necessarily formed as a continuous annular shape and, depending on the shape of the folding regions 35 of the filter 30, the groove part 230A may be formed, for example, in a shape in which the middle of the ring is separated. The supporting member 70 is preferably formed of a member having elasticity. Specifically, a material having a Young's modulus of 0.2 GPa to 2 GPa and an elongation of 50% to 100% is preferably used for the supporting member 70. As such a material, polyethylene or polypropylene is preferable.

Figure 22:
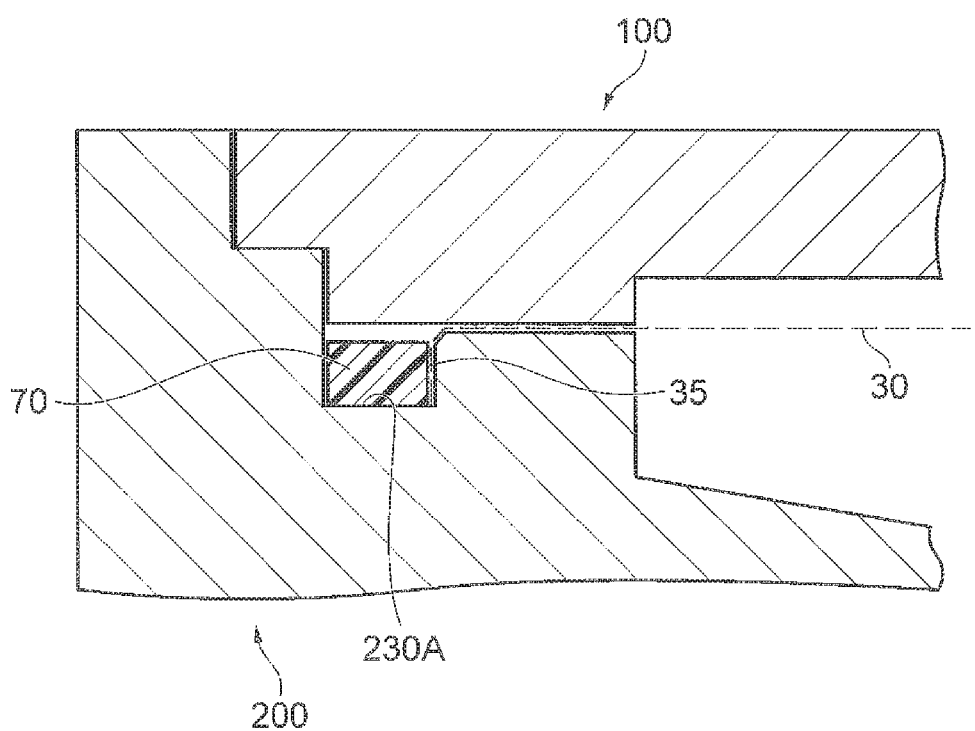
FIG. 22 is a schematic sectional view illustrating the configuration of other modified example of the cell trapping device.

In the above embodiment using the supporting member 70, an embodiment in which the first fitting part 130 is completely removed may be employed. In addition, as illustrated in FIG. 22, an embodiment in which the first protrusion part 125 and the second protrusion part 225 are removed may be employed. In the embodiment illustrated in FIG. 22, a gasket is not used. However, an embodiment in which a gasket is used may be employed. The embodiment in which a gasket is used is preferable because of excellent liquid-tight properties. At this time, an installation of the first protrusion part and the second protrusion part illustrated in FIG. 13 to the lid member 100 and the storage member 200 is more preferable because of more excellent liquid-tight properties. The above embodiment is described using an example in which the storage member 200 is provided with the groove part 230A. The groove part 230A may be provided in the lid member 100.

Also, another embodiment may be employed for the fastening member 60. FIG. 23(A) is the perspective view of a fastening member 60A. FIG. 23(B) is the front view of the fastening member 60A. FIG. 23(C) is the view of the C-C sectional view of the fastening member 60A. As illustrated in FIGS. 23(A) to (C), the part of the fastening member 60A extending in the thickness direction of the housing 10 at the time of equipping to the housing 10 is hollow. Specifically, in the fastening member 60A, each of the hollow part 62 is formed at the aforementioned parts in both sliding directions. The hollow parts 62 preserve a thickness in such a degree that the inside of the fastening member 60A does not communicate with each other as a bottom part 63 and the bottomed holes are formed.

(Cell Trapping System)

Figure 24:
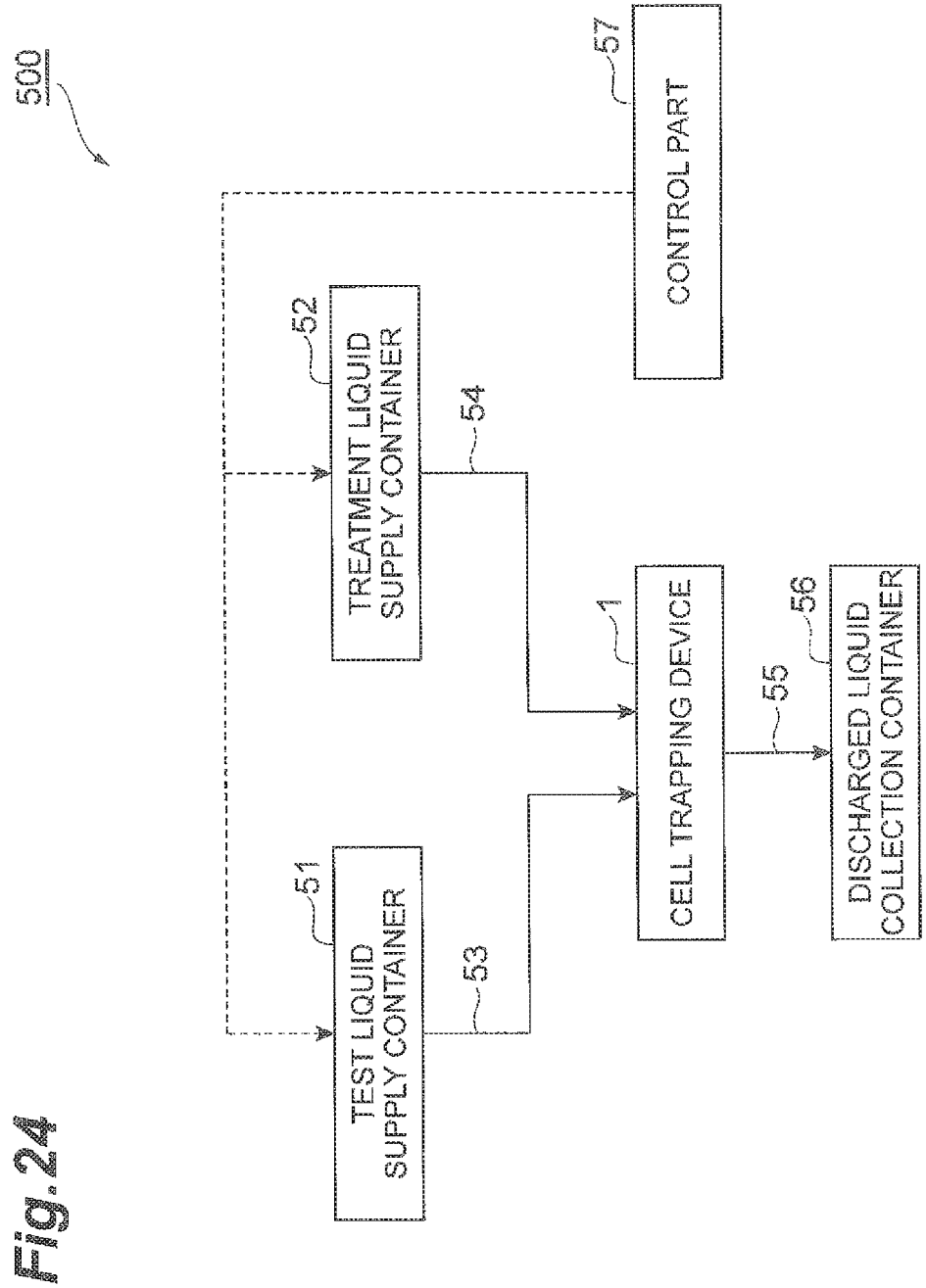
FIG. 24 is a block diagram illustrating the configuration of a cell trapping system.

Subsequently, the cell trapping system using the cell trapping device 1 will be described. FIG. 24 is a block diagram illustrating the configuration of the cell trapping system. As illustrated in FIG. 24, the cell trapping system 500 is configured to include the cell trapping device 1, a test liquid supply container 51 (means for test liquid supply) and a treatment liquid supply container 52 (means for treatment liquid supply) reserving the test liquid and the treatment liquid that are supplied through each of the two introduction channels included in the cell trapping device 1, a test liquid supply channel 53 (means for test liquid supply) connecting the test liquid supply container 51 and the cell trapping device 1, a treatment liquid supply channel 54 (means for treatment liquid supply) connecting the treatment liquid supply container 52 and the cell trapping device 1, a discharge channel 55 connected to the discharge channel included in the cell trapping device 1 and flowing the discharged liquid discharged from the discharge channel to the outside, a discharged liquid collection container 56 connected to the a discharge channel 55 and collecting the discharged liquid, and a control part 57 (means for selection) selecting the liquid to be supplied to the cell trapping device 1 from the test liquid and the treatment liquid and controlling the channel switching and other operations.

The control of the channel switching and the like are carried out by the control part 57. Specific examples of the method for switching the channel may include a method for opening and closing the channel opening and closing valve of the cell trapping device 1. Liquid transfer in the cell trapping system 500 is preferably carried out by, for example, installing a peristaltic pump or the like to the channel. The example in which the one treatment liquid is used is described. However, the configuration in which a plurality of treatment liquid supply containers 52 are provided and the control part 57 controls the choice of treatment liquid to be supplied to the cell trapping device 1 may also be employed.

As described above, the cell trapping system 500 can effectively carry out the trapping process of the cells in the test liquid compared with the conventional systems by having the configuration in which the liquid to be supplied to the cell trapping device 1 is selected by the control part 57 and, based on this result, the test liquid or the treatment liquid is supplied to the cell trapping device 1. In the cell trapping system 500 using the cell trapping device, after the trapping process of the cells, presence or absence of the cells can be observed with improved workability by directly putting the cell trapping device on the observation stage without disassembling the cell trapping device.

Hereinafter, the action of the present embodiments will be described. Conventional cell trapping device tend to have poor repeatability of the support balance of the filter in each fastening because, with regard to the fastening of the lid member and the storage member of the conventional cell trapping device, for example, four sides are fastened with screws or the lid member and the storage member are clamped by pressure with clamps in Patent Literature 2. On the other hand, in the cell trapping device 1 of the present embodiment, the lid member 100 and the storage member 200 are fastened by the fastening members 60A to 60D from both sides in the intersecting direction that is the direction intersecting with the filter 30. The fastening members 60A to 60D fasten the filter 30 by a predetermined load through the peripheral edge part of the housing 10 so as to surround the filter 30 and thus the repeatability of the support balance of the filter 30 is improved. In particular, the cell trapping device 1 illustrated in FIG. 1 can clamp the four-side peripheral edge part of the lid member 100 and the storage member 200 with more uniform load and thus the cell trapping device 1 is more excellent than the cell trapping device 1A illustrated in FIG. 18 in which two-side peripheral edge part is clamped.

In the stage of taking out the detected cells from the device, when the lid member and the storage member are jointed, the impact is applied to the filter at the time of detaching the lid member from the storage member and thus the risk of the scatter of the cells trapped in the filter may exist. On the other hand, in the cell trapping device 1, the lid member 100 is easily separated from the storage member 200 by detaching the fastening members 60 and thus the impact applied to the filter 30 can be reduced at the time of detaching the lid member 100 from the storage member 200. This reduces the risk of the scatter of the cells trapped in the filter. In other words, it can be said that disassembly of the cell trapping device 1 is easy in such a degree that the disassembly does not cause the trouble in the workability at the collection stage of the cells.

The lid member 100 and the storage member 200 have the lid member side guide parts 151 and the storage member side guide parts 251, respectively, and the fastening members 60 have claws engaging these parts. This allows the fastening members 60 to be attached and detached only in the direction along the guide parts 151 and 251 and thus unexpected detachment of the fastening members 60 can be prevented.

In the cell trapping device 1 configured as described above, the filter 30 is fastened by the first protrusion part 125 of the lid member 100 and the second protrusion part 225 of the storage member 200 and the outer circumference part of the filter 30 is clamped with the first fitting part 130 and the second fitting part 230 located further outside being fitted. This results in fastening the filter 30 between the lid member 100 and the storage member 200 with the filter 30 being pulled from the center of the filter 30 the outward direction and thus the filter 30 does not generate wrinkles. Consequently, the cells contained in the test liquid passing through the inside of the filter region 33 can be suitably trapped.

In addition, the filter 30 is sandwiched by the first protrusion part 125 and the second protrusion part 225 from the both sides at the position to be the outer circumference part side of the filter region 33 and thus the introduction channels 101 and 102, the introduction region 120, the discharge region 220 and the discharge channel 201 are blocked from the outside and diffusion of the liquid through the filter 30 and the like in the cell trapping device 1 can be prevented to prevent the seepage of the liquid to the outside, when the liquid (test liquid or treatment liquid) is introduced to the inside of the cell trapping device 1. The cell trapping device 1 maintains excellent liquid-tight properties of the housing 10 because the cell trapping device 1 has the sealing members 40.

When the above effects are tried to be achieved, the surface touching to the filter 30 is preferably a plane shape in the first protrusion part 125 of the lid member 100 and the second protrusion part 225 of the storage member 200. The touch of the surface in the form of the plane surface to the filter 30 allows the liquid to be effectively sealed by surface pressure. The plane view shapes of the first protrusion part 125 of the lid member 100 and the second protrusion part 225 of the storage member 200 whose surfaces are plane surfaces are preferably a quadrilateral shape, a circle shape, an ellipse shape, and a polygonal shape. In order to apply uniform tension, a regular polygonal shape or a circle shape, which is a symmetric shape, is more preferable.

As described above, the embodiments of the present invention are described. The present invention, however, is not limited to the above embodiments and various modifications can be carried out. For example, although the shapes of the lid member and the storage member are determined to be the approximately square shapes, the shapes may be a pentagon shape, a hexagon shape, or other polygonal shapes, or may be a circle shape or an ellipse shape. In the above embodiments, the correspondence between the fastening members and the guide parts is determined to be 1:1. However, a plurality of fastening members can be equipped to one guide part.

In the above embodiments, the guide parts are determined to be the protrusion. However, an embodiment in which the guide part is determined to be a groove and the claws of the fastening member are engaged to the groove may be employed. In this case, the guide parts can be provided without increase in the thickness of the whole housing. In addition, an embodiment in which the guide parts are provided to either the lid member or the storage member may be employed.

The embodiments of the fastening member is not limited to the fastening member having U shape section and a fastening member having other shape can be employed. For example, a shape in which the tips of the U shape approximate each other in such a degree that claws are touched with each other or a shape in which the fastening member has no claws may be employed.

REFERENCE SIGNS LIST

1 . . . Cell Trapping Device, 10 . . . Housing, 30 . . . Filter, 36 . . . Alignment Hole, 40 . . . Sealing Member (Gasket), 60 . . . Fastening Member, 70 . . . Supporting Member, 100 . . . Lid Member, 101, 102 . . . Introduction Channel, 120 . . . Introduction Region, 125 . . . First Protrusion Part, 130 . . . First Fitting Part, 151 . . . Lid Member Side Guide Part, 200 . . . Storage member, 201 . . . Discharge Channel, 220 . . . Discharge Region, 225 . . . Second Protrusion Part, 230 . . . Second Fitting Part, 230A . . . Groove Part, 240 . . . Bottomed Hole (Hole Part), 251 . . . Storage member Side Guide Part, 500 . . . Cell Trapping System.

The invention claimed is:
1. A cell trapping device configured to trap cells in a test liquid comprising:
a housing including
a lid member made of a material translucent to light having a visable wavelength and having an introduction channel configured to introduce a test liquid into an inside, and an introduction region, the introduction channel extending from outside the housing to the introduction region in a horizontal direction and being connected to the introduction region at a portion adjacent a peripheral edge of the introduction region; and
a storage member having a discharge channel configured to discharge the test liquid to an outside;
a filter having a filter region in which at least one through-hole configured to pass the test liquid is formed in a thickness direction, the filter being provided in a channel between the introduction channel and the discharge channel in the housing, and being supported between the lid member and the storage member by the lid member and the storage member; and
a plurality of fastening members configured to clamp the lid member and the storage member from both sides in an intersecting direction that is a direction intersecting with the filter to fasten the lid member and the storage member to each other, wherein
the fastening members are located along a peripheral edge part of the housing so as to surround the filter, and
the introduction region is provided above the filter region.
2. The cell trapping device according to claim 1, wherein
at least one of the lid member and the storage member includes guide parts extending along an outer edge of a surface at a peripheral edge part of the surface to be an outer surface in the intersecting directions at the time of assembly,
the fastening members include claws protruding from a surface facing to the surface including the guide parts, and
the fastening members are configured to be slidable along the guide parts by engaging the claws with the guide parts.
3. The cell trapping device according to claim 2, wherein the guide parts are protrusions.
4. The cell trapping device according to claim 2, wherein the guide parts are grooves.
5. The cell trapping device according to claim 1, further comprising a supporting member configured to support the filter between the lid member and the storage member, wherein
the lid member or the storage member has a groove having a depth in the intersecting direction at a position of an outer side from the filter region at the time of assembly,
the supporting member has a shape that allows the supporting member to be accommodated in the groove, and
the supporting member accommodated in the lid member or the storage member supports the filter by pressing the filter to the groove side of the lid member or the storage member at an outer circumference side from the filter region.
6. The cell trapping device according to claim 1, wherein the lid member includes:
a first protrusion part provided at a position outward from the filter region and inward from an outer edge of the filter at the time of assembly and to protrude outward from a surface of a side to which the filter is attached; and
a first fitting part provided at a position outward away from the first protrusion part and a position where at least a part of the filter is overlapped at the time of assembly and configured to fit with the storage member, the storage member includes:
- a second protrusion part provided at a position corresponding to the first protrusion part at the time of assembly and located at a position corresponding to the first protrusion part to protrude; and
- a second fitting part configured to fit with the lid part at the time of assembly, one of the first fitting part and the second fitting part has a convex shape and the other has a concave shape, and the channel is formed inside the housing by locating the first protrusion part and the second protrusion part at a corresponding position sandwiching the filter and the filter is fastened by fitting the first fitting part and the second fitting part at an outer circumference side from the filter region is preferable.

7. The cell trapping device according to claim 6, further comprising a sealing member configured to be sandwiched between the filter and at least one of the first protrusion part and the second protrusion part and to have elasticity, wherein the sealing member is located at all regions corresponding to the first protrusion part and the second protrusion part in a state of sandwiching the filter.

8. The cell trapping device according to claim 1, wherein an outer surface of the storage member protrudes in the intersecting direction, compared with an edge part of the storage member side of the fastening members.

9. The cell trapping device according to claim 1, wherein an outer surface of the lid member protrudes in the intersecting direction, compared with an edge part of the lid member side of the fastening members.

10. The cell trapping device according to claim 1, wherein a length of the fastening members in the intersecting direction is equal to or less than the thickness of the housing.

11. The cell trapping device according to claim 1, wherein
the filter in the cell trapping device has a plurality of alignment holes at positions outward from the filter region and inward from an outer edge of the filter, and
at least one of the lid member and the storage member has hole parts provided at positions corresponding to the alignment holes.

12. The cell trapping device according to claim 1, wherein the test liquid is blood, and
the trapped cells are circulating tumor cells.

13. A cell trapping system comprising:
the cell trapping device according to claim 1;
test liquid supplying means for supplying the test liquid to the introduction channel of the cell trapping device;
treatment liquid supplying means for supplying the treatment liquid for treating the cells trapped in the filter to the introduction channel of the cell trapping device by passing the treatment liquid through the filter; and
selecting means for selecting the liquid to supply to the cell trapping device from the test liquid and the treatment liquid.

14. The cell trapping device according to claim 1, wherein the introduction channel is connected to a corner of the introduction region.

15. A method for producing a cell trapping device, the cell trapping device comprising:
a housing including
a lid member made of a material translucent to light having a visible wavelength and having an introduction channel configured to introduce a test liquid into an inside, and an introduction region, the introduction channel extending from outside the housing to the introduction region in a horizontal direction and being connected to the introduction region at a portion adjacent a peripheral edge of the introduction region; and
a storage member having a discharge channel configured to discharge the test liquid to an outside;
a filter having a filter region in which a through-hole configured to pass the test liquid is formed in a thickness direction, provided on a channel between the introduction channel and the discharge channel in the housing, and supported between the lid member and the storage member by the lid member and the storage member; and
a plurality of fastening members configured to clamp the lid member and the storage member from both sides in an intersecting direction that is a direction intersecting with the filter to fasten the lid member and the storage member to each other, wherein
the introduction region is provided above the filter region,
the method comprising:
overlapping the storage member, the filter, and the lid member; and
clamping the peripheral part of the housing by the fastening members so as to surround the filter.

16. The method for producing a cell trapping device according to claim 15, wherein
the filter having a plurality of alignment holes at positions outward from the filter region and inward from an outer edge of the filter,
at least one of the lid member and the storage member having hole parts provided at positions corresponding to the alignment holes, and
the method comprises aligning the lid member or the storage member and the filter by inserting stick-like jigs whose edge parts are inserted into the hole parts through the alignment holes at the time of overlapping the filter with the lid member or the storage member.

17. The method for producing a cell trapping device according to claim 15, wherein
the introduction channel is connected to a corner of the introduction region.

* * * * *